US012582485B2

(12) United States Patent
Rafii-Tari et al.

(10) Patent No.: US 12,582,485 B2
(45) Date of Patent: ***Mar. 24, 2026

(54) MULTIPLE-INPUT INSTRUMENT POSITION DETERMINATION

(71) Applicant: Auris Health, Inc., Santa Clara, CA (US)

(72) Inventors: Hedyeh Rafii-Tari, Mountain View, CA (US); Ritwik Ummalaneni, San Mateo, CA (US); Simon Wei Quan Lim, San Mateo, CA (US); Prasanth Jeevan, San Mateo, CA (US)

(73) Assignee: Auris Health, Inc., Santa Clara, CA (US)

( * ) Notice: Subject to any disclaimer, the term of this patent is extended or adjusted under 35 U.S.C. 154(b) by 461 days.

This patent is subject to a terminal disclaimer.

(21) Appl. No.: 17/978,841

(22) Filed: Nov. 1, 2022

(65) Prior Publication Data

US 2023/0049292 A1 Feb. 16, 2023

Related U.S. Application Data

(63) Continuation of application No. 16/219,766, filed on Dec. 13, 2018, now Pat. No. 11,510,736.
(Continued)

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/30* (2016.02); *A61B 34/70* (2016.02);
(Continued)

(58) Field of Classification Search
CPC ......... A61B 34/20; A61B 34/30; A61B 34/70; A61B 2034/2051; A61B 2034/2055;
(Continued)

(56) References Cited

U.S. PATENT DOCUMENTS

| | | | |
|---|---|---|---|
| 2,556,601 A | 6/1951 | Schofield | |
| 2,566,183 A | 8/1951 | Forss | |

(Continued)

FOREIGN PATENT DOCUMENTS

| | | | |
|---|---|---|---|
| CN | 1364275 A | 8/2002 | |
| CN | 1511249 A | 7/2004 | |

(Continued)

OTHER PUBLICATIONS

Notice of Allowance for Appl. No. 10-2018-7028120, dated Feb. 21, 2023, 1 page.
(Continued)

*Primary Examiner* — Baisakhi Roy
(74) *Attorney, Agent, or Firm* — Paradice & Li LLP

(57) ABSTRACT

A robotic system includes an instrument including an elongate shaft, a robotic manipulator configured to manipulate the elongate shaft of the instrument, and control circuitry communicatively coupled to the robotic manipulator and configured to determine a first estimated position of at least a portion of the elongate shaft of the instrument based at least in part on robotic command data, determine a second estimated position of the at least a portion of the elongate shaft of the instrument based at least in part on position sensor data, compare the first estimated position and the second estimated position, and generate a third estimated position based at least in part on the comparison of the first estimated position to the second estimated position.

20 Claims, 20 Drawing Sheets

Related U.S. Application Data

(60) Provisional application No. 62/598,934, filed on Dec. 14, 2017.

(51) Int. Cl.
     *A61B 34/30*          (2016.01)
     *A61B 17/00*          (2006.01)
     *A61B 90/00*          (2016.01)

(52) U.S. Cl.
     CPC .............. *A61B 2017/00398* (2013.01); *A61B 2034/2051* (2016.02); *A61B 2034/2055* (2016.02); *A61B 2034/2061* (2016.02); *A61B 2034/301* (2016.02); *A61B 2090/0811* (2016.02); *A61B 2090/0818* (2016.02); *A61B 90/361* (2016.02)

(58) Field of Classification Search
     CPC ...... A61B 2034/2061; A61B 2034/301; A61B 2090/0811; A61B 2090/0818; A61B 90/361
     See application file for complete search history.

(56)                    References Cited

U.S. PATENT DOCUMENTS

| | | |
|---|---|---|
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Niitu et al. |
| 3,790,002 A | 2/1974 | Guilbaud et al. |
| 3,921,536 A | 11/1975 | Savage |
| 3,926,386 A | 12/1975 | Stahmann et al. |
| 4,115,869 A | 9/1978 | Putnam et al. |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,644,237 A | 2/1987 | Frushour et al. |
| 4,688,555 A | 8/1987 | Wardle |
| 4,745,908 A | 5/1988 | Wardle |
| 4,748,969 A | 6/1988 | Wardle |
| 4,784,150 A | 11/1988 | Voorhies et al. |
| 4,857,058 A | 8/1989 | W. |
| 4,907,168 A | 3/1990 | Boggs |
| 4,945,790 A | 8/1990 | Golden |
| 5,194,791 A | 3/1993 | Cull |
| 5,207,128 A | 5/1993 | Albright |
| 5,234,428 A | 8/1993 | Kaufman |
| 5,251,611 A | 10/1993 | Zehel et al. |
| 5,256,150 A | 10/1993 | Quiachon et al. |
| 5,273,025 A | 12/1993 | Sakiyama et al. |
| 5,277,085 A | 1/1994 | Tanimura et al. |
| 5,280,781 A | 1/1994 | Oku |
| 5,350,101 A | 9/1994 | Godlewski |
| 5,408,263 A | 4/1995 | Kikuchi et al. |
| 5,426,687 A | 6/1995 | Goodall et al. |
| 5,507,725 A | 4/1996 | Savage et al. |
| 5,524,180 A | 6/1996 | Wang et al. |
| 5,526,812 A | 6/1996 | Dumoulin et al. |
| 5,550,953 A | 8/1996 | Seraji |
| 5,559,294 A | 9/1996 | Hoium et al. |
| 5,672,877 A | 9/1997 | Liebig et al. |
| 5,709,661 A | 1/1998 | Egmond et al. |
| 5,767,840 A | 6/1998 | Selker |
| 5,769,086 A | 6/1998 | Ritchart et al. |
| 5,779,623 A | 7/1998 | Bonnell |
| 5,792,135 A | 8/1998 | Madhani et al. |
| 5,797,900 A | 8/1998 | Madhani et al. |
| 5,831,614 A | 11/1998 | Tognazzini et al. |
| 5,842,390 A | 12/1998 | Bouligny et al. |
| 5,855,583 A | 1/1999 | Wang et al. |
| 5,899,851 A | 5/1999 | Koninckx |
| 5,921,968 A | 7/1999 | Lampropoulos et al. |
| 5,935,075 A | 8/1999 | Casscells et al. |
| 5,967,934 A | 10/1999 | Ishida et al. |
| 6,004,016 A | 12/1999 | Spector |
| 6,038,467 A | 3/2000 | Bliek et al. |
| 6,047,080 A | 4/2000 | Chen et al. |
| 6,059,718 A | 5/2000 | Taniguchi et al. |
| 6,063,095 A | 5/2000 | Wang et al. |
| 6,077,219 A | 6/2000 | Viebach et al. |
| 6,084,371 A | 7/2000 | Kress et al. |
| 6,154,000 A | 11/2000 | Rastegar et al. |
| 6,167,292 A | 12/2000 | Badano et al. |
| 6,171,234 B1 | 1/2001 | White et al. |
| 6,185,478 B1 | 2/2001 | Koakutsu et al. |
| 6,198,974 B1 | 3/2001 | Webster, Jr. |
| 6,203,493 B1 | 3/2001 | Ben-Haim |
| 6,246,200 B1 | 6/2001 | Blumenkranz et al. |
| 6,246,784 B1 | 6/2001 | Summers et al. |
| 6,246,898 B1 | 6/2001 | Vesely et al. |
| 6,272,371 B1 | 8/2001 | Shlomo |
| 6,289,579 B1 | 9/2001 | Viza et al. |
| 6,332,089 B1 | 12/2001 | Acker et al. |
| 6,394,998 B1 | 5/2002 | Wallace et al. |
| 6,401,572 B1 | 6/2002 | Provost |
| 6,425,865 B1 | 7/2002 | Salcudean et al. |
| 6,436,107 B1 | 8/2002 | Wang et al. |
| 6,459,926 B1 | 10/2002 | Nowlin et al. |
| 6,466,198 B1 | 10/2002 | Feinstein |
| 6,487,940 B2 | 12/2002 | Hart et al. |
| 6,490,467 B1 | 12/2002 | Bucholz et al. |
| 6,491,701 B2 | 12/2002 | Tierney et al. |
| 6,553,251 B1 | 4/2003 | Lähdesmäki |
| 6,665,554 B1 | 12/2003 | Charles et al. |
| 6,690,963 B2 | 2/2004 | Ben-Haim et al. |
| 6,690,964 B2 | 2/2004 | Bieger et al. |
| 6,695,818 B2 | 2/2004 | Wollschläger |
| 6,726,675 B1 | 4/2004 | Beyar |
| 6,755,797 B1 * | 6/2004 | Stouffer ................ A61H 23/04 |
| | | 601/149 |
| 6,786,896 B1 | 9/2004 | Madhani et al. |
| 6,812,842 B2 | 11/2004 | Dimmer |
| 6,827,712 B2 | 12/2004 | Tovey et al. |
| 6,837,846 B2 | 1/2005 | Jaffe et al. |
| 6,899,672 B2 | 5/2005 | Chin et al. |
| 6,926,709 B2 | 8/2005 | Bieger et al. |
| 7,044,936 B2 | 5/2006 | Harding et al. |
| 7,172,580 B2 | 2/2007 | Hruska et al. |
| 7,180,976 B2 | 2/2007 | Wink et al. |
| 7,197,354 B2 | 3/2007 | Sobe |
| 7,206,627 B2 | 4/2007 | Abovitz et al. |
| 7,233,820 B2 | 6/2007 | Gilboa |
| 7,276,044 B2 | 10/2007 | Ferry et al. |
| 7,386,339 B2 | 6/2008 | Strommer et al. |
| 7,607,440 B2 | 10/2009 | Coste-Maniere et al. |
| 7,615,042 B2 | 11/2009 | Beyar et al. |
| 7,635,342 B2 | 12/2009 | Ferry et al. |
| 7,756,563 B2 | 7/2010 | Higgins et al. |
| 7,763,015 B2 | 7/2010 | Cooper et al. |
| 7,766,856 B2 | 8/2010 | Ferry et al. |
| 7,772,541 B2 | 8/2010 | Froggatt et al. |
| 7,850,642 B2 | 12/2010 | Moll et al. |
| 7,901,348 B2 | 3/2011 | Soper et al. |
| 7,930,065 B2 | 4/2011 | Larkin et al. |
| 7,938,809 B2 | 5/2011 | Lampropoulos et al. |
| 7,963,288 B2 | 6/2011 | Rosenberg et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,155,403 B2 | 4/2012 | Tschirren et al. |

(56)  References Cited

U.S. PATENT DOCUMENTS

| | | | |
|---|---|---|---|
| 8,157,308 B2 | 4/2012 | Pedersen | |
| 8,182,415 B2 | 5/2012 | Larkin et al. | |
| 8,190,238 B2 | 5/2012 | Moll et al. | |
| 8,277,417 B2 | 10/2012 | Fedinec | |
| 8,291,791 B2 | 10/2012 | Light et al. | |
| 8,298,135 B2 | 10/2012 | Ito et al. | |
| 8,317,746 B2 | 11/2012 | Sewell et al. | |
| 8,335,557 B2 | 12/2012 | Maschke | |
| 8,348,931 B2 | 1/2013 | Cooper et al. | |
| 8,376,934 B2 | 2/2013 | Takahashi et al. | |
| 8,394,054 B2 | 3/2013 | Wallace et al. | |
| 8,396,595 B2 | 3/2013 | Dariush | |
| 8,414,505 B1 | 4/2013 | Weitzner et al. | |
| 8,425,465 B2 | 4/2013 | Nagano et al. | |
| 8,442,618 B2 | 5/2013 | Strommer et al. | |
| 8,460,236 B2 | 6/2013 | Roelle et al. | |
| 8,469,945 B2 | 6/2013 | Schena | |
| 8,498,691 B2 | 7/2013 | Moll et al. | |
| 8,506,555 B2 | 8/2013 | Morales | |
| 8,554,368 B2 | 10/2013 | Fielding et al. | |
| 8,671,817 B1 | 3/2014 | Bogusky | |
| 8,720,448 B2 | 5/2014 | Reis et al. | |
| 8,738,181 B2 | 5/2014 | Greer et al. | |
| 8,746,252 B2 | 6/2014 | McGrogan et al. | |
| 8,821,376 B2 | 9/2014 | Tolkowsky | |
| 8,827,948 B2 | 9/2014 | Romo et al. | |
| 8,858,424 B2 | 10/2014 | Hasegawa et al. | |
| 8,870,815 B2 | 10/2014 | Bhat et al. | |
| 8,894,610 B2 | 11/2014 | Macnamara et al. | |
| 8,929,631 B2 | 1/2015 | Pfister et al. | |
| 8,945,095 B2 | 2/2015 | Blumenkranz et al. | |
| 8,961,533 B2 | 2/2015 | Stahler et al. | |
| 8,968,333 B2 | 3/2015 | Yu et al. | |
| 8,992,542 B2 | 3/2015 | Hagag et al. | |
| 9,014,851 B2 | 4/2015 | Wong et al. | |
| 9,023,060 B2 | 5/2015 | Cooper et al. | |
| 9,084,623 B2 * | 7/2015 | Gomez | B25J 9/1679 |
| 9,125,639 B2 | 9/2015 | Mathis et al. | |
| 9,125,690 B2 * | 9/2015 | Wohlgemuth | A61B 34/30 |
| 9,129,417 B2 | 9/2015 | Zheng et al. | |
| 9,138,129 B2 | 9/2015 | Diolaiti | |
| 9,173,713 B2 | 11/2015 | Hart et al. | |
| 9,183,354 B2 | 11/2015 | Baker et al. | |
| 9,186,046 B2 | 11/2015 | Ramamurthy et al. | |
| 9,199,372 B2 | 12/2015 | Henderson et al. | |
| 9,204,933 B2 | 12/2015 | Reis et al. | |
| 9,226,796 B2 | 1/2016 | Bowling et al. | |
| 9,256,940 B2 | 2/2016 | Carelsen et al. | |
| 9,259,281 B2 | 2/2016 | Griffiths et al. | |
| 9,272,416 B2 * | 3/2016 | Hourtash | A61B 34/37 |
| 9,289,578 B2 | 3/2016 | Walker et al. | |
| 9,302,702 B1 | 4/2016 | Schepmann et al. | |
| 9,314,306 B2 | 4/2016 | Yu | |
| 9,326,822 B2 | 5/2016 | Lewis et al. | |
| 9,345,456 B2 | 5/2016 | Tsonton et al. | |
| 9,358,682 B2 | 6/2016 | Morales | |
| 9,408,669 B2 | 8/2016 | Kokish et al. | |
| 9,446,177 B2 | 9/2016 | Millman et al. | |
| 9,452,018 B2 | 9/2016 | Yu | |
| 9,452,276 B2 | 9/2016 | Duindam et al. | |
| 9,457,168 B2 | 10/2016 | Moll et al. | |
| 9,459,087 B2 | 10/2016 | Dunbar et al. | |
| 9,498,601 B2 | 11/2016 | Tanner et al. | |
| 9,504,604 B2 | 11/2016 | Alvarez | |
| 9,522,034 B2 | 12/2016 | Johnson et al. | |
| 9,561,083 B2 | 2/2017 | Yu et al. | |
| 9,603,668 B2 | 3/2017 | Weingarten et al. | |
| 9,622,827 B2 | 4/2017 | Yu et al. | |
| 9,629,595 B2 | 4/2017 | Walker et al. | |
| 9,629,682 B2 | 4/2017 | Wallace et al. | |
| 9,636,184 B2 | 5/2017 | Lee et al. | |
| 9,636,483 B2 | 5/2017 | Hart et al. | |
| 9,668,814 B2 | 6/2017 | Kokish | |
| 9,675,422 B2 | 6/2017 | Hourtash et al. | |
| 9,710,921 B2 | 7/2017 | Wong et al. | |
| 9,713,509 B2 | 7/2017 | Schuh et al. | |
| 9,717,563 B2 | 8/2017 | Tognaccini et al. | |
| 9,726,476 B2 | 8/2017 | Ramamurthy et al. | |
| 9,727,963 B2 * | 8/2017 | Mintz | A61B 1/00149 |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,789,608 B2 | 10/2017 | Itkowitz et al. | |
| 9,802,317 B1 * | 10/2017 | Watts | G05B 19/402 |
| 9,818,681 B2 | 11/2017 | Machida | |
| 9,844,353 B2 | 12/2017 | Walker et al. | |
| 9,844,412 B2 | 12/2017 | Bogusky et al. | |
| 9,867,635 B2 | 1/2018 | Alvarez et al. | |
| 9,918,659 B2 | 3/2018 | Chopra et al. | |
| 9,918,681 B2 | 3/2018 | Wallace et al. | |
| 9,931,025 B1 | 4/2018 | Graetzel et al. | |
| 9,936,972 B2 | 4/2018 | Blohm et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 9,993,614 B2 | 6/2018 | Pacheco et al. | |
| 10,016,900 B1 | 7/2018 | Meyer et al. | |
| 10,019,566 B1 * | 7/2018 | Gallagher | B25J 9/1666 |
| 10,022,192 B1 | 7/2018 | Ummalaneni | |
| 10,046,140 B2 | 8/2018 | Kokish et al. | |
| 10,080,576 B2 | 9/2018 | Romo et al. | |
| 10,098,701 B2 | 10/2018 | Tsusaka et al. | |
| 10,123,755 B2 | 11/2018 | Walker et al. | |
| 10,130,345 B2 | 11/2018 | Wong et al. | |
| 10,136,950 B2 | 11/2018 | Schoenefeld | |
| 10,136,959 B2 | 11/2018 | Mintz et al. | |
| 10,143,360 B2 | 12/2018 | Roelle et al. | |
| 10,143,526 B2 | 12/2018 | Walker et al. | |
| 10,145,747 B1 | 12/2018 | Lin et al. | |
| 10,149,720 B2 | 12/2018 | Romo | |
| 10,159,532 B1 | 12/2018 | Ummalaneni | |
| 10,159,533 B2 | 12/2018 | Moll et al. | |
| 10,169,875 B2 | 1/2019 | Mintz et al. | |
| 10,213,264 B2 | 2/2019 | Tanner et al. | |
| 10,219,874 B2 | 3/2019 | Yu et al. | |
| 10,231,793 B2 * | 3/2019 | Romo | A61B 1/0676 |
| 10,231,867 B2 | 3/2019 | Alvarez et al. | |
| 10,244,926 B2 | 4/2019 | Noonan et al. | |
| 10,258,285 B2 | 4/2019 | Hauck et al. | |
| 10,278,778 B2 | 5/2019 | State et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,383,765 B2 | 8/2019 | Alvarez et al. | |
| 10,398,518 B2 | 9/2019 | Yu et al. | |
| 10,405,939 B2 | 9/2019 | Romo | |
| 10,405,940 B2 | 9/2019 | Romo | |
| 10,426,559 B2 * | 10/2019 | Graetzel | A61B 34/71 |
| 10,426,661 B2 | 10/2019 | Kintz | |
| 10,434,660 B2 | 10/2019 | Meyer et al. | |
| 10,454,347 B2 | 10/2019 | Covington et al. | |
| 10,464,209 B2 | 11/2019 | Ho et al. | |
| 10,470,830 B2 | 11/2019 | Hill et al. | |
| 10,478,595 B2 | 11/2019 | Kokish | |
| 10,482,599 B2 | 11/2019 | Mintz et al. | |
| 10,492,741 B2 | 12/2019 | Walker et al. | |
| 10,493,239 B2 | 12/2019 | Hart et al. | |
| 10,493,241 B2 | 12/2019 | Jiang | |
| 10,500,001 B2 | 12/2019 | Yu et al. | |
| 10,517,692 B2 | 12/2019 | Eyre et al. | |
| 10,524,866 B2 | 1/2020 | Srinivasan et al. | |
| 10,524,867 B2 | 1/2020 | Kokish et al. | |
| 10,531,864 B2 | 1/2020 | Wong et al. | |
| 10,539,478 B2 | 1/2020 | Lin et al. | |
| 10,543,047 B2 | 1/2020 | Yu | |
| 10,543,048 B2 | 1/2020 | Noonan | |
| 10,555,778 B2 * | 2/2020 | Ummalaneni | A61G 13/10 |
| 10,556,092 B2 | 2/2020 | Yu et al. | |
| 10,569,052 B2 | 2/2020 | Kokish et al. | |
| 10,582,974 B2 | 3/2020 | Zhao et al. | |

(56) References Cited

U.S. PATENT DOCUMENTS

| | | | |
|---|---|---|---|
| 10,638,953 B2 | 5/2020 | Duindam et al. | |
| 10,639,114 B2 | 5/2020 | Schuh et al. | |
| 10,667,875 B2* | 6/2020 | DeFonzo | A61B 90/361 |
| 10,743,751 B2 | 8/2020 | Landey et al. | |
| 10,751,140 B2* | 8/2020 | Wallace | A61B 34/30 |
| 10,765,487 B2 | 9/2020 | Ho et al. | |
| 11,510,736 B2* | 11/2022 | Rafii-Tari | A61B 34/70 |
| 11,771,309 B2 | 10/2023 | Noonan | |
| 2001/0000040 A1 | 3/2001 | Adams et al. | |
| 2001/0021843 A1 | 9/2001 | Bosselmann et al. | |
| 2001/0039421 A1 | 11/2001 | Heilbrun et al. | |
| 2001/0042643 A1 | 11/2001 | Krueger et al. | |
| 2002/0032452 A1* | 3/2002 | Tierney | G06Q 30/02 |
| | | | 606/130 |
| 2002/0035330 A1 | 3/2002 | Cline et al. | |
| 2002/0045905 A1 | 4/2002 | Gerbi et al. | |
| 2002/0065455 A1 | 5/2002 | Ben-Haim et al. | |
| 2002/0077533 A1 | 6/2002 | Bieger et al. | |
| 2002/0098938 A1 | 7/2002 | Milbourne et al. | |
| 2002/0100254 A1 | 8/2002 | Dharssi | |
| 2002/0107573 A1 | 8/2002 | Steinberg | |
| 2002/0117017 A1 | 8/2002 | Bernhardt et al. | |
| 2002/0120188 A1 | 8/2002 | Brock et al. | |
| 2002/0161280 A1 | 10/2002 | Chatenever et al. | |
| 2002/0161355 A1 | 10/2002 | Wollschlager | |
| 2002/0161426 A1 | 10/2002 | Iancea | |
| 2002/0173878 A1 | 11/2002 | Watanabe et al. | |
| 2002/0177789 A1 | 11/2002 | Ferry et al. | |
| 2003/0045778 A1 | 3/2003 | Ohline et al. | |
| 2003/0056561 A1 | 3/2003 | Butscher et al. | |
| 2003/0105603 A1 | 6/2003 | Hardesty | |
| 2003/0125622 A1 | 7/2003 | Schweikard et al. | |
| 2003/0167623 A1 | 9/2003 | Lorenz | |
| 2003/0181809 A1 | 9/2003 | Hall et al. | |
| 2003/0182091 A1 | 9/2003 | Kukuk | |
| 2003/0195664 A1 | 10/2003 | Nowlin et al. | |
| 2003/0212308 A1 | 11/2003 | Bendall | |
| 2004/0015053 A1 | 1/2004 | Bieger et al. | |
| 2004/0047044 A1 | 3/2004 | Dalton | |
| 2004/0072066 A1 | 4/2004 | Cho et al. | |
| 2004/0076940 A1* | 4/2004 | Alexander | G09B 23/285 |
| | | | 434/262 |
| 2004/0152972 A1 | 8/2004 | Hunter | |
| 2004/0186349 A1 | 9/2004 | Ewers et al. | |
| 2004/0243147 A1 | 12/2004 | Lipow | |
| 2004/0249267 A1 | 12/2004 | Gilboa | |
| 2004/0254566 A1 | 12/2004 | Plicchi et al. | |
| 2004/0257021 A1 | 12/2004 | Chang et al. | |
| 2004/0263535 A1 | 12/2004 | Birkenbach et al. | |
| 2005/0004579 A1 | 1/2005 | Schneider et al. | |
| 2005/0027397 A1 | 2/2005 | Niemeyer | |
| 2005/0043718 A1 | 2/2005 | Madhani et al. | |
| 2005/0060006 A1 | 3/2005 | Pflueger et al. | |
| 2005/0065400 A1 | 3/2005 | Banik et al. | |
| 2005/0085714 A1 | 4/2005 | Foley et al. | |
| 2005/0107679 A1 | 5/2005 | Geiger et al. | |
| 2005/0107917 A1 | 5/2005 | Smith et al. | |
| 2005/0143649 A1 | 6/2005 | Minai et al. | |
| 2005/0143655 A1* | 6/2005 | Satoh | G06T 5/73 |
| | | | 600/443 |
| 2005/0177026 A1 | 8/2005 | Hoeg et al. | |
| 2005/0182295 A1 | 8/2005 | Soper et al. | |
| 2005/0183532 A1 | 8/2005 | Najafi et al. | |
| 2005/0193451 A1* | 9/2005 | Quistgaard | A61B 34/76 |
| | | | 901/9 |
| 2005/0222554 A1 | 10/2005 | Wallace et al. | |
| 2005/0234293 A1 | 10/2005 | Yamamoto et al. | |
| 2005/0256398 A1* | 11/2005 | Hastings | A61B 34/73 |
| | | | 600/410 |
| 2005/0261551 A1 | 11/2005 | Couvillon, Jr. et al. | |
| 2005/0272975 A1 | 12/2005 | McWeeney et al. | |
| 2006/0004286 A1 | 1/2006 | Chang et al. | |
| 2006/0015096 A1 | 1/2006 | Hauck et al. | |
| 2006/0025668 A1 | 2/2006 | Peterson et al. | |
| 2006/0041245 A1 | 2/2006 | Ferry et al. | |
| 2006/0041293 A1 | 2/2006 | Mehdizadeh et al. | |
| 2006/0058643 A1 | 3/2006 | Florent et al. | |
| 2006/0079745 A1 | 4/2006 | Viswanathan | |
| 2006/0084860 A1 | 4/2006 | Geiger et al. | |
| 2006/0095066 A1 | 5/2006 | Chang et al. | |
| 2006/0098851 A1 | 5/2006 | Shoham et al. | |
| 2006/0111692 A1 | 5/2006 | Hlavka et al. | |
| 2006/0146010 A1 | 7/2006 | Schneider | |
| 2006/0149134 A1 | 7/2006 | Soper et al. | |
| 2006/0173290 A1 | 8/2006 | Lavallee et al. | |
| 2006/0184016 A1 | 8/2006 | Glossop | |
| 2006/0200026 A1 | 9/2006 | Wallace et al. | |
| 2006/0200049 A1 | 9/2006 | Leo et al. | |
| 2006/0201688 A1 | 9/2006 | Jenner et al. | |
| 2006/0209019 A1* | 9/2006 | Hu | G06F 3/016 |
| | | | 345/156 |
| 2006/0229587 A1 | 10/2006 | Beyar et al. | |
| 2006/0237205 A1 | 10/2006 | Sia et al. | |
| 2006/0258935 A1 | 11/2006 | Pile-Spellman et al. | |
| 2006/0258938 A1 | 11/2006 | Hoffman et al. | |
| 2007/0000498 A1 | 1/2007 | Glynn et al. | |
| 2007/0013336 A1 | 1/2007 | Nowlin et al. | |
| 2007/0032826 A1 | 2/2007 | Schwartz | |
| 2007/0043455 A1 | 2/2007 | Viswanathan et al. | |
| 2007/0055128 A1 | 3/2007 | Glossop | |
| 2007/0055144 A1 | 3/2007 | Neustadter et al. | |
| 2007/0060879 A1 | 3/2007 | Weitzner et al. | |
| 2007/0073136 A1 | 3/2007 | Metzger | |
| 2007/0083193 A1 | 4/2007 | Werneth et al. | |
| 2007/0100201 A1 | 5/2007 | Komiya et al. | |
| 2007/0100254 A1 | 5/2007 | Murakami et al. | |
| 2007/0112355 A1 | 5/2007 | Salahieh et al. | |
| 2007/0119274 A1 | 5/2007 | Devengenzo et al. | |
| 2007/0123748 A1 | 5/2007 | Meglan | |
| 2007/0135886 A1 | 6/2007 | Maschke | |
| 2007/0142971 A1 | 6/2007 | Schena et al. | |
| 2007/0149946 A1 | 6/2007 | Viswanathan et al. | |
| 2007/0150155 A1 | 6/2007 | Kawai et al. | |
| 2007/0156019 A1 | 7/2007 | Larkin et al. | |
| 2007/0167743 A1 | 7/2007 | Honda et al. | |
| 2007/0167801 A1 | 7/2007 | Webler et al. | |
| 2007/0185485 A1 | 8/2007 | Hauck et al. | |
| 2007/0191177 A1 | 8/2007 | Nagai et al. | |
| 2007/0208252 A1 | 9/2007 | Makower | |
| 2007/0239028 A1 | 10/2007 | Houser et al. | |
| 2007/0245175 A1 | 10/2007 | Zheng et al. | |
| 2007/0249911 A1 | 10/2007 | Simon | |
| 2007/0253599 A1 | 11/2007 | White et al. | |
| 2007/0265527 A1 | 11/2007 | Wohlgemuth | |
| 2007/0269001 A1 | 11/2007 | Maschke | |
| 2007/0287992 A1 | 12/2007 | Diolaiti et al. | |
| 2007/0293721 A1 | 12/2007 | Gilboa | |
| 2007/0299353 A1 | 12/2007 | Harlev et al. | |
| 2007/0299427 A1 | 12/2007 | Yeung et al. | |
| 2008/0027313 A1 | 1/2008 | Shachar | |
| 2008/0039255 A1 | 2/2008 | Jinno et al. | |
| 2008/0046122 A1 | 2/2008 | Manzo et al. | |
| 2008/0064921 A1 | 3/2008 | Larkin et al. | |
| 2008/0065103 A1 | 3/2008 | Cooper et al. | |
| 2008/0071140 A1 | 3/2008 | Gattani et al. | |
| 2008/0079421 A1 | 4/2008 | Jensen | |
| 2008/0103389 A1 | 5/2008 | Begelman et al. | |
| 2008/0108870 A1 | 5/2008 | Wiita et al. | |
| 2008/0118118 A1 | 5/2008 | Berger | |
| 2008/0118135 A1 | 5/2008 | Averbuch et al. | |
| 2008/0123921 A1 | 5/2008 | Gielen et al. | |
| 2008/0140087 A1 | 6/2008 | Barbagli | |
| 2008/0147011 A1 | 6/2008 | Urmey | |
| 2008/0147089 A1 | 6/2008 | Loh et al. | |
| 2008/0159653 A1 | 7/2008 | Dunki-Jacobs et al. | |
| 2008/0161681 A1 | 7/2008 | Hauck | |
| 2008/0177285 A1 | 7/2008 | Brock et al. | |
| 2008/0183064 A1 | 7/2008 | Chandonnet et al. | |
| 2008/0183068 A1 | 7/2008 | Carls et al. | |
| 2008/0183073 A1 | 7/2008 | Higgins et al. | |
| 2008/0183188 A1 | 7/2008 | Carls et al. | |
| 2008/0201016 A1 | 8/2008 | Finlay | |
| 2008/0207997 A1 | 8/2008 | Higgins et al. | |

(56)                    References Cited

U.S. PATENT DOCUMENTS

| | | |
|---|---|---|
| 2008/0212082 A1 | 9/2008 | Froggatt et al. |
| 2008/0214925 A1 | 9/2008 | Wilson et al. |
| 2008/0218770 A1 | 9/2008 | Moll et al. |
| 2008/0231221 A1 | 9/2008 | Ogawa |
| 2008/0243064 A1 | 10/2008 | Stahler et al. |
| 2008/0243142 A1 | 10/2008 | Gildenberg |
| 2008/0249536 A1 | 10/2008 | Stahler et al. |
| 2008/0249640 A1 | 10/2008 | Vittor et al. |
| 2008/0253108 A1 | 10/2008 | Ellenburg et al. |
| 2008/0255505 A1 | 10/2008 | Carlson et al. |
| 2008/0262297 A1 | 10/2008 | Gilboa et al. |
| 2008/0262301 A1 | 10/2008 | Gibbons et al. |
| 2008/0275349 A1 | 11/2008 | Halperin et al. |
| 2008/0287963 A1 | 11/2008 | Rogers et al. |
| 2008/0302200 A1 | 12/2008 | Tobey |
| 2008/0306490 A1 | 12/2008 | Lakin et al. |
| 2008/0312501 A1 | 12/2008 | Hasegawa et al. |
| 2008/0312771 A1 | 12/2008 | Sugiura |
| 2009/0005768 A1 | 1/2009 | Sharareh et al. |
| 2009/0030307 A1 | 1/2009 | Govari et al. |
| 2009/0054729 A1 | 2/2009 | Mori et al. |
| 2009/0062813 A1 | 3/2009 | Prisco et al. |
| 2009/0076476 A1 | 3/2009 | Barbagli et al. |
| 2009/0076534 A1 | 3/2009 | Shelton et al. |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0137952 A1 | 5/2009 | Ramamurthy et al. |
| 2009/0149867 A1 | 6/2009 | Glozman et al. |
| 2009/0163948 A1 | 6/2009 | Sunaoshi et al. |
| 2009/0165580 A1 | 7/2009 | Fisher et al. |
| 2009/0171371 A1 | 7/2009 | Nixon et al. |
| 2009/0184825 A1 | 7/2009 | Anderson |
| 2009/0198298 A1 | 8/2009 | Kaiser et al. |
| 2009/0227861 A1 | 9/2009 | Ganatra et al. |
| 2009/0245600 A1 | 10/2009 | Hoffman et al. |
| 2009/0247944 A1 | 10/2009 | Kirschenman et al. |
| 2009/0248036 A1 | 10/2009 | Hoffman et al. |
| 2009/0248039 A1 | 10/2009 | Cooper et al. |
| 2009/0256905 A1 | 10/2009 | Tashiro |
| 2009/0259230 A1 | 10/2009 | Khadem et al. |
| 2009/0262109 A1 | 10/2009 | Markowitz et al. |
| 2009/0271036 A1* | 10/2009 | Kock ..................... B25J 9/1666 |
| | | 700/245 |
| 2009/0287354 A1 | 11/2009 | Choi |
| 2009/0292166 A1 | 11/2009 | Ito et al. |
| 2009/0295797 A1 | 12/2009 | Sakaguchi |
| 2009/0324161 A1 | 12/2009 | Prisco |
| 2010/0008555 A1 | 1/2010 | Trumer et al. |
| 2010/0030023 A1 | 2/2010 | Yoshie |
| 2010/0030061 A1 | 2/2010 | Canfield et al. |
| 2010/0030115 A1 | 2/2010 | Fujimoto et al. |
| 2010/0039506 A1 | 2/2010 | Sarvestani et al. |
| 2010/0041949 A1 | 2/2010 | Tolkowsky |
| 2010/0054536 A1 | 3/2010 | Huang et al. |
| 2010/0057099 A1 | 3/2010 | Fujimoto et al. |
| 2010/0069833 A1 | 3/2010 | Wenderow et al. |
| 2010/0069920 A1 | 3/2010 | Naylor et al. |
| 2010/0073150 A1 | 3/2010 | Olson et al. |
| 2010/0076263 A1 | 3/2010 | Tanaka et al. |
| 2010/0113852 A1 | 5/2010 | Sydora |
| 2010/0121138 A1 | 5/2010 | Goldenberg et al. |
| 2010/0121139 A1 | 5/2010 | OuYang et al. |
| 2010/0130923 A1 | 5/2010 | Cleary et al. |
| 2010/0130987 A1 | 5/2010 | Wenderow et al. |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0168562 A1 | 7/2010 | Zhao et al. |
| 2010/0168918 A1 | 7/2010 | Zhao et al. |
| 2010/0175701 A1 | 7/2010 | Reis et al. |
| 2010/0204646 A1 | 8/2010 | Plicchi et al. |
| 2010/0204713 A1 | 8/2010 | Morales |
| 2010/0210923 A1 | 8/2010 | Li et al. |
| 2010/0225209 A1 | 9/2010 | Goldberg et al. |
| 2010/0228266 A1 | 9/2010 | Hourtash |
| 2010/0234856 A1 | 9/2010 | Stoianovici et al. |
| 2010/0240989 A1 | 9/2010 | Stoianovici et al. |
| 2010/0248177 A1 | 9/2010 | Mangelberger et al. |
| 2010/0249506 A1 | 9/2010 | Prisco |
| 2010/0256812 A1 | 10/2010 | Tsusaka et al. |
| 2010/0274078 A1 | 10/2010 | Kim et al. |
| 2010/0290530 A1 | 11/2010 | Huang et al. |
| 2010/0292565 A1 | 11/2010 | Meyer et al. |
| 2010/0298641 A1 | 11/2010 | Tanaka |
| 2010/0328455 A1 | 12/2010 | Nam et al. |
| 2010/0332033 A1 | 12/2010 | Diolaiti et al. |
| 2011/0009880 A1 | 1/2011 | Prisco et al. |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0021926 A1 | 1/2011 | Spencer et al. |
| 2011/0028991 A1 | 2/2011 | Ikeda et al. |
| 2011/0054303 A1 | 3/2011 | Barrick et al. |
| 2011/0082366 A1 | 4/2011 | Scully et al. |
| 2011/0082462 A1 | 4/2011 | Suarez et al. |
| 2011/0092808 A1 | 4/2011 | Shachar et al. |
| 2011/0130718 A1 | 6/2011 | Kidd et al. |
| 2011/0137122 A1 | 6/2011 | Kawai |
| 2011/0147030 A1 | 6/2011 | Blum et al. |
| 2011/0152880 A1 | 6/2011 | Alvarez et al. |
| 2011/0153252 A1 | 6/2011 | Govari et al. |
| 2011/0160570 A1 | 6/2011 | Kariv et al. |
| 2011/0184238 A1 | 7/2011 | Higgins et al. |
| 2011/0196199 A1 | 8/2011 | Donhowe et al. |
| 2011/0208000 A1 | 8/2011 | Honda et al. |
| 2011/0218676 A1 | 9/2011 | Okazaki |
| 2011/0234780 A1 | 9/2011 | Ito et al. |
| 2011/0238082 A1 | 9/2011 | Wenderow et al. |
| 2011/0238083 A1 | 9/2011 | Moll et al. |
| 2011/0245665 A1 | 10/2011 | Nentwick |
| 2011/0248987 A1 | 10/2011 | Mitchell |
| 2011/0249016 A1* | 10/2011 | Zhang ...................... H04N 9/67 |
| | | 345/589 |
| 2011/0257480 A1* | 10/2011 | Takahashi .......... A61B 1/00147 |
| | | 600/106 |
| 2011/0258842 A1 | 10/2011 | Dukesherer et al. |
| 2011/0261183 A1 | 10/2011 | Ma et al. |
| 2011/0264038 A1 | 10/2011 | Fujimoto et al. |
| 2011/0276179 A1 | 11/2011 | Banks et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2011/0319815 A1 | 12/2011 | Roelle et al. |
| 2011/0319910 A1 | 12/2011 | Roelle et al. |
| 2012/0000427 A1 | 1/2012 | Nilsson |
| 2012/0046521 A1 | 2/2012 | Hunter et al. |
| 2012/0046522 A1 | 2/2012 | Naito |
| 2012/0056986 A1 | 3/2012 | Popovic |
| 2012/0059249 A1 | 3/2012 | Verard et al. |
| 2012/0062714 A1 | 3/2012 | Liu et al. |
| 2012/0065481 A1 | 3/2012 | Hunter et al. |
| 2012/0069167 A1 | 3/2012 | Liu et al. |
| 2012/0071752 A1 | 3/2012 | Sewell et al. |
| 2012/0071782 A1 | 3/2012 | Patil et al. |
| 2012/0071821 A1 | 3/2012 | Yu |
| 2012/0071822 A1 | 3/2012 | Romo et al. |
| 2012/0071894 A1 | 3/2012 | Tanner et al. |
| 2012/0071895 A1 | 3/2012 | Stahler et al. |
| 2012/0082351 A1 | 4/2012 | Higgins et al. |
| 2012/0120305 A1 | 5/2012 | Takahashi |
| 2012/0123441 A1 | 5/2012 | Au et al. |
| 2012/0130217 A1 | 5/2012 | Kauphusman et al. |
| 2012/0132018 A1 | 5/2012 | Tang et al. |
| 2012/0143226 A1 | 6/2012 | Belson et al. |
| 2012/0150154 A1 | 6/2012 | Brisson et al. |
| 2012/0165656 A1 | 6/2012 | Montag et al. |
| 2012/0186194 A1 | 7/2012 | Schlieper |
| 2012/0191079 A1 | 7/2012 | Moll et al. |
| 2012/0191107 A1 | 7/2012 | Tanner et al. |
| 2012/0203168 A1 | 8/2012 | Fujimoto et al. |
| 2012/0209069 A1 | 8/2012 | Popovic et al. |
| 2012/0209293 A1 | 8/2012 | Carlson et al. |
| 2012/0215094 A1 | 8/2012 | Rahimian et al. |

(56) References Cited

U.S. PATENT DOCUMENTS

| | | |
|---|---|---|
| 2012/0219185 A1 | 8/2012 | Hu et al. |
| 2012/0232476 A1 | 9/2012 | Bhat et al. |
| 2012/0239012 A1 | 9/2012 | Laurent et al. |
| 2012/0253276 A1 | 10/2012 | Govari et al. |
| 2012/0277730 A1 | 11/2012 | Salahieh et al. |
| 2012/0283745 A1 | 11/2012 | Goldberg et al. |
| 2012/0283747 A1 | 11/2012 | Popovic |
| 2012/0289777 A1 | 11/2012 | Chopra et al. |
| 2012/0289783 A1 | 11/2012 | Duindam et al. |
| 2012/0302869 A1 | 11/2012 | Koyrakh et al. |
| 2012/0328077 A1 | 12/2012 | Bouvier |
| 2013/0018306 A1 | 1/2013 | Ludwin |
| 2013/0018400 A1 | 1/2013 | Milton et al. |
| 2013/0060146 A1 | 3/2013 | Yang et al. |
| 2013/0066335 A1 | 3/2013 | Bärwinkel et al. |
| 2013/0085330 A1 | 4/2013 | Ramamurthy et al. |
| 2013/0090530 A1 | 4/2013 | Ramamurthy et al. |
| 2013/0102846 A1 | 4/2013 | Sjostrom et al. |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle et al. |
| 2013/0204124 A1 | 8/2013 | Duindam et al. |
| 2013/0218005 A1 | 8/2013 | Desai et al. |
| 2013/0225942 A1 | 8/2013 | Holsing et al. |
| 2013/0231678 A1 | 9/2013 | Wenderow et al. |
| 2013/0243153 A1 | 9/2013 | Sra et al. |
| 2013/0246334 A1 | 9/2013 | Ahuja et al. |
| 2013/0259315 A1 | 10/2013 | Angot et al. |
| 2013/0303891 A1 | 11/2013 | Chopra et al. |
| 2013/0303892 A1 | 11/2013 | Zhao et al. |
| 2013/0304084 A1 | 11/2013 | Beira et al. |
| 2013/0317519 A1 | 11/2013 | Romo et al. |
| 2013/0325030 A1 | 12/2013 | Hourtash et al. |
| 2013/0345519 A1 | 12/2013 | Piskun et al. |
| 2013/0345718 A1 | 12/2013 | Crawford et al. |
| 2014/0000411 A1 | 1/2014 | Shelton, IV et al. |
| 2014/0058406 A1 | 2/2014 | Tsekos |
| 2014/0066944 A1 | 3/2014 | Taylor et al. |
| 2014/0069437 A1 | 3/2014 | Reis et al. |
| 2014/0107390 A1 | 4/2014 | Brown et al. |
| 2014/0114180 A1 | 4/2014 | Jain et al. |
| 2014/0135985 A1 | 5/2014 | Coste-Maniere et al. |
| 2014/0142591 A1 | 5/2014 | Alvarez et al. |
| 2014/0148808 A1 | 5/2014 | Inkpen et al. |
| 2014/0163664 A1 | 6/2014 | Goldsmith |
| 2014/0166023 A1 | 6/2014 | Kishi |
| 2014/0171778 A1 | 6/2014 | Tsusaka et al. |
| 2014/0180063 A1 | 6/2014 | Zhao et al. |
| 2014/0222019 A1 | 8/2014 | Brudniok |
| 2014/0222207 A1 | 8/2014 | Bowling et al. |
| 2014/0235943 A1 | 8/2014 | Paris et al. |
| 2014/0243849 A1 | 8/2014 | Saglam et al. |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0276937 A1 | 9/2014 | Wong et al. |
| 2014/0277333 A1 | 9/2014 | Lewis et al. |
| 2014/0277334 A1 | 9/2014 | Yu et al. |
| 2014/0296655 A1 | 10/2014 | Akhbardeh et al. |
| 2014/0296657 A1* | 10/2014 | Izmirli ................. A61B 5/061 |
| | | 600/301 |
| 2014/0296870 A1 | 10/2014 | Stern et al. |
| 2014/0309527 A1 | 10/2014 | Namati et al. |
| 2014/0309649 A1 | 10/2014 | Alvarez et al. |
| 2014/0316420 A1 | 10/2014 | Ballard et al. |
| 2014/0343416 A1 | 11/2014 | Panescu et al. |
| 2014/0343569 A1 | 11/2014 | Turner |
| 2014/0350391 A1 | 11/2014 | Prisco et al. |
| 2014/0357984 A1 | 12/2014 | Wallace et al. |
| 2014/0364739 A1 | 12/2014 | Liu et al. |
| 2014/0364870 A1 | 12/2014 | Alvarez et al. |
| 2014/0375784 A1 | 12/2014 | Massetti |
| 2014/0379000 A1 | 12/2014 | Romo et al. |
| 2015/0012134 A1 | 1/2015 | Robinson et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto et al. |
| 2015/0073266 A1 | 3/2015 | Brannan et al. |
| 2015/0073267 A1 | 3/2015 | Brannan et al. |
| 2015/0088161 A1 | 3/2015 | Hata et al. |
| 2015/0090063 A1 | 4/2015 | Lantermann et al. |
| 2015/0101442 A1 | 4/2015 | Romo |
| 2015/0104284 A1 | 4/2015 | Riedel et al. |
| 2015/0119628 A1 | 4/2015 | Bharat et al. |
| 2015/0119637 A1 | 4/2015 | Alvarez et al. |
| 2015/0119638 A1 | 4/2015 | Yu et al. |
| 2015/0133963 A1 | 5/2015 | Barbagli |
| 2015/0141808 A1 | 5/2015 | Elhawary et al. |
| 2015/0141858 A1 | 5/2015 | Razavi et al. |
| 2015/0142013 A1 | 5/2015 | Tanner et al. |
| 2015/0144514 A1 | 5/2015 | Brannan et al. |
| 2015/0148600 A1 | 5/2015 | Ashinuma et al. |
| 2015/0150635 A1 | 6/2015 | Kilroy et al. |
| 2015/0164594 A1 | 6/2015 | Romo et al. |
| 2015/0164596 A1 | 6/2015 | Romo et al. |
| 2015/0182250 A1 | 7/2015 | Conlon et al. |
| 2015/0202015 A1 | 7/2015 | Elhawary et al. |
| 2015/0223725 A1 | 8/2015 | Engel et al. |
| 2015/0223897 A1 | 8/2015 | Kostrzewski et al. |
| 2015/0223902 A1 | 8/2015 | Walker et al. |
| 2015/0231364 A1 | 8/2015 | Blanchard et al. |
| 2015/0255782 A1 | 9/2015 | Kim et al. |
| 2015/0265087 A1 | 9/2015 | Messick, Jr. |
| 2015/0265359 A1 | 9/2015 | Camarillo |
| 2015/0265368 A1 | 9/2015 | Chopra et al. |
| 2015/0265807 A1 | 9/2015 | Park et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0297864 A1* | 10/2015 | Kokish .................. A61B 34/37 |
| | | 604/95.04 |
| 2015/0305650 A1 | 10/2015 | Hunter et al. |
| 2015/0311838 A1 | 10/2015 | Moule et al. |
| 2015/0313503 A1* | 11/2015 | Seibel .................... A61B 5/065 |
| | | 600/103 |
| 2015/0327939 A1 | 11/2015 | Kokish et al. |
| 2015/0335480 A1 | 11/2015 | Alvarez et al. |
| 2015/0342695 A1 | 12/2015 | He et al. |
| 2015/0359597 A1 | 12/2015 | Gombert et al. |
| 2015/0374445 A1 | 12/2015 | Gombert et al. |
| 2015/0374956 A1 | 12/2015 | Bogusky |
| 2016/0000302 A1 | 1/2016 | Brown et al. |
| 2016/0000414 A1 | 1/2016 | Brown et al. |
| 2016/0000495 A1 | 1/2016 | Elliott et al. |
| 2016/0000512 A1 | 1/2016 | Gombert et al. |
| 2016/0000520 A1 | 1/2016 | Lachmanovich et al. |
| 2016/0001038 A1 | 1/2016 | Romo et al. |
| 2016/0005168 A1 | 1/2016 | Merlet |
| 2016/0005220 A1 | 1/2016 | Weingarten et al. |
| 2016/0005576 A1 | 1/2016 | Tsukamoto |
| 2016/0008033 A1 | 1/2016 | Hawkins et al. |
| 2016/0016319 A1 | 1/2016 | Remirez et al. |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper et al. |
| 2016/0075030 A1 | 3/2016 | Takahashi et al. |
| 2016/0081568 A1 | 3/2016 | Kolberg et al. |
| 2016/0100772 A1 | 4/2016 | Ikuma et al. |
| 2016/0111192 A1 | 4/2016 | Suzara |
| 2016/0128992 A1 | 5/2016 | Hudson et al. |
| 2016/0135908 A1 | 5/2016 | Takahashi et al. |
| 2016/0157945 A1 | 6/2016 | Madhani et al. |
| 2016/0166234 A1 | 6/2016 | Zhang et al. |
| 2016/0183841 A1 | 6/2016 | Duindam et al. |

(56) References Cited

U.S. PATENT DOCUMENTS

| | | | |
|---|---|---|---|
| 2016/0192860 A1 | 7/2016 | Allenby et al. | |
| 2016/0199134 A1 | 7/2016 | Brown et al. | |
| 2016/0206389 A1 | 7/2016 | Miller et al. | |
| 2016/0213432 A1 | 7/2016 | Flexman et al. | |
| 2016/0213435 A1 | 7/2016 | Hourtash et al. | |
| 2016/0228032 A1 | 8/2016 | Walker et al. | |
| 2016/0235946 A1 | 8/2016 | Lewis et al. | |
| 2016/0270865 A1 | 9/2016 | Landey et al. | |
| 2016/0278865 A1 | 9/2016 | Capote et al. | |
| 2016/0287053 A1 | 10/2016 | Miura et al. | |
| 2016/0287111 A1 | 10/2016 | Jacobsen et al. | |
| 2016/0287279 A1 | 10/2016 | Bovay et al. | |
| 2016/0287346 A1 | 10/2016 | Hyodo et al. | |
| 2016/0314710 A1* | 10/2016 | Jarc | G09B 23/285 |
| 2016/0331469 A1 | 11/2016 | Hall et al. | |
| 2016/0338783 A1 | 11/2016 | Romo et al. | |
| 2016/0338785 A1 | 11/2016 | Kokish et al. | |
| 2016/0338787 A1 | 11/2016 | Popovic et al. | |
| 2016/0346038 A1 | 12/2016 | Helgeson et al. | |
| 2016/0346049 A1 | 12/2016 | Allen et al. | |
| 2016/0346924 A1 | 12/2016 | Hasegawa et al. | |
| 2016/0349044 A1 | 12/2016 | Marell et al. | |
| 2016/0354057 A1 | 12/2016 | Hansen et al. | |
| 2016/0354582 A1 | 12/2016 | Yu et al. | |
| 2016/0360947 A1 | 12/2016 | Iida et al. | |
| 2016/0360949 A1 | 12/2016 | Hyodo et al. | |
| 2016/0372743 A1 | 12/2016 | Cho et al. | |
| 2016/0374541 A1 | 12/2016 | Agrawal et al. | |
| 2017/0007337 A1 | 1/2017 | Dan | |
| 2017/0007343 A1 | 1/2017 | Yu | |
| 2017/0055851 A1 | 3/2017 | Al-Ali et al. | |
| 2017/0056215 A1 | 3/2017 | Nagesh et al. | |
| 2017/0065364 A1 | 3/2017 | Schuh et al. | |
| 2017/0065365 A1 | 3/2017 | Schuh | |
| 2017/0068796 A1 | 3/2017 | Passerini et al. | |
| 2017/0071684 A1 | 3/2017 | Kokish et al. | |
| 2017/0079725 A1 | 3/2017 | Hoffman et al. | |
| 2017/0079726 A1 | 3/2017 | Hoffman et al. | |
| 2017/0084027 A1* | 3/2017 | Mintz | A61B 5/061 |
| 2017/0095143 A1 | 4/2017 | Sato et al. | |
| 2017/0100197 A1 | 4/2017 | Zubiate et al. | |
| 2017/0100199 A1 | 4/2017 | Yu et al. | |
| 2017/0105804 A1 | 4/2017 | Yu | |
| 2017/0106904 A1 | 4/2017 | Hanson et al. | |
| 2017/0119413 A1 | 5/2017 | Romo | |
| 2017/0119481 A1 | 5/2017 | Romo et al. | |
| 2017/0119484 A1 | 5/2017 | Tanner et al. | |
| 2017/0151027 A1* | 6/2017 | Walker | A61B 34/37 |
| 2017/0151028 A1 | 6/2017 | Ogawa et al. | |
| 2017/0165011 A1 | 6/2017 | Bovay et al. | |
| 2017/0165503 A1 | 6/2017 | Hautvast et al. | |
| 2017/0172673 A1 | 6/2017 | Yu et al. | |
| 2017/0189118 A1 | 7/2017 | Chopra et al. | |
| 2017/0202627 A1 | 7/2017 | Sramek et al. | |
| 2017/0209073 A1 | 7/2017 | Sramek et al. | |
| 2017/0209672 A1 | 7/2017 | Hart et al. | |
| 2017/0215808 A1 | 8/2017 | Shimol et al. | |
| 2017/0215969 A1 | 8/2017 | Zhai et al. | |
| 2017/0238807 A9 | 8/2017 | Vertikov | |
| 2017/0245854 A1 | 8/2017 | Zemlok et al. | |
| 2017/0245885 A1 | 8/2017 | Lenker et al. | |
| 2017/0251988 A1 | 9/2017 | Weber et al. | |
| 2017/0252540 A1 | 9/2017 | Weitzner et al. | |
| 2017/0258366 A1 | 9/2017 | Tupin, Jr. et al. | |
| 2017/0258534 A1 | 9/2017 | Hourtash et al. | |
| 2017/0280978 A1 | 10/2017 | Yamamoto et al. | |
| 2017/0281049 A1 | 10/2017 | Yamamoto et al. | |
| 2017/0290631 A1 | 10/2017 | Lee et al. | |
| 2017/0296032 A1 | 10/2017 | Li | |
| 2017/0296202 A1 | 10/2017 | Brown | |
| 2017/0296784 A1 | 10/2017 | Kokish | |
| 2017/0303889 A1 | 10/2017 | Grim et al. | |
| 2017/0303941 A1 | 10/2017 | Eisner | |
| 2017/0304015 A1 | 10/2017 | Tavallaei et al. | |
| 2017/0312481 A1 | 11/2017 | Covington et al. | |
| 2017/0325715 A1 | 11/2017 | Mehendale et al. | |
| 2017/0325896 A1 | 11/2017 | Donhowe et al. | |
| 2017/0325932 A1 | 11/2017 | Hoelzle | |
| 2017/0333679 A1 | 11/2017 | Jiang | |
| 2017/0340241 A1 | 11/2017 | Yamada | |
| 2017/0340396 A1 | 11/2017 | Romo et al. | |
| 2017/0348067 A1 | 12/2017 | Krimsky | |
| 2017/0360508 A1 | 12/2017 | Germain et al. | |
| 2017/0365055 A1 | 12/2017 | Mintz et al. | |
| 2017/0367782 A1 | 12/2017 | Schuh et al. | |
| 2018/0025666 A1 | 1/2018 | Ho et al. | |
| 2018/0042464 A1 | 2/2018 | Arai et al. | |
| 2018/0042686 A1 | 2/2018 | Peine | |
| 2018/0049792 A1 | 2/2018 | Eckert et al. | |
| 2018/0055576 A1* | 3/2018 | Koyrakh | A61B 5/113 |
| 2018/0055582 A1 | 3/2018 | Krimsky | |
| 2018/0056044 A1 | 3/2018 | Choi et al. | |
| 2018/0064498 A1 | 3/2018 | Kapadia et al. | |
| 2018/0098690 A1 | 4/2018 | Iwaki | |
| 2018/0104820 A1 | 4/2018 | Troy et al. | |
| 2018/0116735 A1 | 5/2018 | Tierney et al. | |
| 2018/0177383 A1 | 6/2018 | Noonan et al. | |
| 2018/0177556 A1 | 6/2018 | Noonan | |
| 2018/0177561 A1 | 6/2018 | Mintz et al. | |
| 2018/0206927 A1 | 7/2018 | Prisco et al. | |
| 2018/0214011 A1 | 8/2018 | Graetzel et al. | |
| 2018/0217734 A1 | 8/2018 | Koenig et al. | |
| 2018/0221038 A1 | 8/2018 | Noonan et al. | |
| 2018/0221039 A1 | 8/2018 | Shah | |
| 2018/0240237 A1 | 8/2018 | Donhowe et al. | |
| 2018/0243048 A1 | 8/2018 | Shan et al. | |
| 2018/0250083 A1 | 9/2018 | Schuh et al. | |
| 2018/0250085 A1 | 9/2018 | Simi et al. | |
| 2018/0271604 A1 | 9/2018 | Grout et al. | |
| 2018/0271616 A1 | 9/2018 | Schuh et al. | |
| 2018/0279852 A1 | 10/2018 | Rafii-Tari et al. | |
| 2018/0280660 A1 | 10/2018 | Landey et al. | |
| 2018/0286108 A1 | 10/2018 | Hirakawa | |
| 2018/0289243 A1 | 10/2018 | Landey et al. | |
| 2018/0289431 A1 | 10/2018 | Draper et al. | |
| 2018/0296299 A1 | 10/2018 | Iceman | |
| 2018/0303566 A1 | 10/2018 | Soundararajan et al. | |
| 2018/0308247 A1 | 10/2018 | Gupta | |
| 2018/0325499 A1 | 11/2018 | Landey et al. | |
| 2018/0326181 A1 | 11/2018 | Kokish et al. | |
| 2018/0333044 A1 | 11/2018 | Jenkins | |
| 2018/0360435 A1 | 12/2018 | Romo | |
| 2018/0368920 A1 | 12/2018 | Ummalaneni | |
| 2019/0000559 A1 | 1/2019 | Berman et al. | |
| 2019/0000560 A1 | 1/2019 | Berman et al. | |
| 2019/0000566 A1 | 1/2019 | Graetzel et al. | |
| 2019/0000568 A1 | 1/2019 | Connolly et al. | |
| 2019/0000576 A1 | 1/2019 | Mintz et al. | |
| 2019/0033971 A1* | 1/2019 | Reynolds | G06F 3/0443 |
| 2019/0046814 A1 | 2/2019 | Senden et al. | |
| 2019/0066314 A1 | 2/2019 | Abhari et al. | |
| 2019/0083183 A1 | 3/2019 | Moll et al. | |
| 2019/0086349 A1 | 3/2019 | Nelson et al. | |
| 2019/0105776 A1 | 4/2019 | Ho et al. | |
| 2019/0105785 A1 | 4/2019 | Meyer et al. | |
| 2019/0107454 A1 | 4/2019 | Lin et al. | |
| 2019/0110839 A1 | 4/2019 | Rafii-Tari et al. | |
| 2019/0110843 A1* | 4/2019 | Ummalaneni | A61B 1/000094 |
| 2019/0121361 A1* | 4/2019 | Afrouzi | G01C 21/206 |
| 2019/0125164 A1 | 5/2019 | Roelle et al. | |
| 2019/0142537 A1 | 5/2019 | Covington | |
| 2019/0151148 A1 | 5/2019 | Alvarez et al. | |
| 2019/0167366 A1 | 6/2019 | Ummalaneni et al. | |
| 2019/0167367 A1 | 6/2019 | Walker et al. | |
| 2019/0175009 A1 | 6/2019 | Mintz et al. | |
| 2019/0175062 A1 | 6/2019 | Rafii-Tari et al. | |
| 2019/0175287 A1 | 6/2019 | Hill et al. | |
| 2019/0175799 A1 | 6/2019 | Hsu et al. | |
| 2019/0183585 A1 | 6/2019 | Rafii-Tari et al. | |
| 2019/0183587 A1 | 6/2019 | Rafii-Tari et al. | |
| 2019/0209252 A1 | 7/2019 | Walker et al. | |
| 2019/0216548 A1 | 7/2019 | Ummalaneni | |
| 2019/0216550 A1 | 7/2019 | Eyre et al. | |
| 2019/0216576 A1 | 7/2019 | Eyre et al. | |

(56)                    References Cited

U.S. PATENT DOCUMENTS

| | | |
|---|---|---|
| 2019/0223967 A1 | 7/2019 | Abbott et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0231458 A1 | 8/2019 | DiMaio et al. |
| 2019/0239723 A1 | 8/2019 | Duindam et al. |
| 2019/0246882 A1 | 8/2019 | Graetzel et al. |
| 2019/0262086 A1 | 8/2019 | Connolly et al. |
| 2019/0269468 A1* | 9/2019 | Hsu .................... A61B 34/20 |
| 2019/0274764 A1 | 9/2019 | Romo |
| 2019/0287673 A1 | 9/2019 | Michihata et al. |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0008874 A1 | 1/2020 | Barbagli et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054405 A1 | 2/2020 | Schuh et al. |
| 2020/0054408 A1 | 2/2020 | Schuh et al. |
| 2020/0060516 A1 | 2/2020 | Baez, Jr. |
| 2020/0078103 A1 | 3/2020 | Duindam et al. |
| 2020/0086087 A1 | 3/2020 | Hart et al. |
| 2020/0091799 A1 | 3/2020 | Covington et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0129252 A1 | 4/2020 | Kokish et al. |
| 2020/0146769 A1 | 5/2020 | Eyre et al. |
| 2020/0155084 A1 | 5/2020 | Walker et al. |
| 2020/0155245 A1 | 5/2020 | Yu |
| 2020/0155801 A1 | 5/2020 | Kokish et al. |
| 2020/0170630 A1 | 6/2020 | Wong et al. |
| 2020/0170720 A1 | 6/2020 | Ummalaneni |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0230360 A1 | 7/2020 | Yu et al. |
| 2020/0237458 A1 | 7/2020 | DeFonzo et al. |
| 2020/0246591 A1 | 8/2020 | Bogusky |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0289023 A1 | 9/2020 | Duindam et al. |

FOREIGN PATENT DOCUMENTS

| | | |
|---|---|---|
| CN | 1846181 A | 10/2006 |
| CN | 1857877 A | 11/2006 |
| CN | 101147676 A | 3/2008 |
| CN | 101161426 A | 4/2008 |
| CN | 101222882 A | 7/2008 |
| CN | 101325920 A | 12/2008 |
| CN | 101500470 A | 8/2009 |
| CN | 102015759 A | 4/2011 |
| CN | 201884596 U | 6/2011 |
| CN | 102316817 A | 1/2012 |
| CN | 102327118 A | 1/2012 |
| CN | 102341055 A | 2/2012 |
| CN | 102458295 A | 5/2012 |
| CN | 102665590 A | 9/2012 |
| CN | 102711586 A | 10/2012 |
| CN | 102834043 A | 12/2012 |
| CN | 102973317 A | 3/2013 |
| CN | 103037799 A | 4/2013 |
| CN | 103533909 A | 1/2014 |
| CN | 103565529 A | 2/2014 |
| CN | 103735313 A | 4/2014 |
| CN | 103767659 A | 5/2014 |
| CN | 103930063 A | 7/2014 |
| CN | 104684502 A | 6/2015 |
| CN | 105030331 A | 11/2015 |
| CN | 105147393 A | 12/2015 |
| CN | 105511881 A | 4/2016 |
| CN | 105559850 A | 5/2016 |
| CN | 105559886 A | 5/2016 |
| CN | 105643642 A | 6/2016 |
| CN | 106821498 A | 6/2017 |
| CN | 107028659 A | 8/2017 |
| CN | 104931059 B | 9/2018 |
| DE | 19649082 C1 | 1/1998 |
| DE | 102004020465 | 9/2005 |
| DE | 102013100605 A1 | 7/2014 |
| EP | 1250986 A2 | 10/2002 |
| EP | 1442720 A1 | 8/2004 |
| EP | 1491139 A2 | 12/2004 |
| EP | 1566150 A2 | 8/2005 |
| EP | 1800593 A1 | 6/2007 |
| EP | 2158834 A1 | 3/2010 |
| EP | 2392435 A2 | 12/2011 |
| EP | 2229892 B1 | 1/2012 |
| EP | 2567670 A1 | 3/2013 |
| EP | 3025630 A1 | 6/2016 |
| EP | 3562423 A1 | 11/2019 |
| JP | 2005205198 A | 8/2005 |
| JP | 2007136173 A | 6/2007 |
| JP | 2007527296 A | 9/2007 |
| JP | 2008528130 A | 7/2008 |
| JP | 2009509654 A | 3/2009 |
| JP | 2009139187 A | 6/2009 |
| JP | 2009524530 A | 7/2009 |
| JP | 2010046384 A | 3/2010 |
| JP | 2011088260 A | 5/2011 |
| JP | 2013510662 A | 3/2013 |
| JP | 2014134530 A | 7/2014 |
| JP | 2015505507 A | 2/2015 |
| JP | 2019529044 A | 10/2019 |
| KR | 20080027256 A | 3/2008 |
| KR | 1020140009359 A | 1/2014 |
| KR | 1020140033128 A | 3/2014 |
| KR | 20150132145 A | 11/2015 |
| KR | 1020150132145 A | 11/2015 |
| RU | 2569699 C2 | 11/2015 |
| WO | 0156457 A1 | 8/2001 |
| WO | 02074178 A2 | 9/2002 |
| WO | 2004029782 A2 | 4/2004 |
| WO | 2005078128 A1 | 8/2005 |
| WO | 2005087128 A1 | 9/2005 |
| WO | 2006122061 A1 | 11/2006 |
| WO | 2006124388 A1 | 11/2006 |
| WO | 2007146987 A2 | 12/2007 |
| WO | 2009092059 A2 | 7/2009 |
| WO | 2009097461 A1 | 8/2009 |
| WO | 2009120940 A2 | 10/2009 |
| WO | 2011005335 A1 | 1/2011 |
| WO | 2011132409 A1 | 10/2011 |
| WO | 2012037506 A2 | 3/2012 |
| WO | 2012044334 A2 | 4/2012 |
| WO | 2012158324 A2 | 11/2012 |
| WO | 2013116140 A1 | 8/2013 |
| WO | 2013179600 A1 | 12/2013 |
| WO | 2014114551 A1 | 7/2014 |
| WO | 2014150509 A1 | 9/2014 |

(56)  References Cited

FOREIGN PATENT DOCUMENTS

| WO | 2015061756 A1 | 4/2015 |
| WO | 2015089013 A1 | 6/2015 |
| WO | 2015127231 A1 | 8/2015 |
| WO | 2015142957 A1 | 9/2015 |
| WO | 2015198773 A1 | 12/2015 |
| WO | 2017048194 A1 | 3/2017 |
| WO | 2017049163 A1 | 3/2017 |
| WO | 2017059412 A1 | 4/2017 |
| WO | 2017066108 A1 | 4/2017 |
| WO | 2017151993 A1 | 9/2017 |
| WO | 2017167754 A1 | 10/2017 |
| WO | 2018057633 A1 | 3/2018 |
| WO | 2018125917 A1 | 7/2018 |

OTHER PUBLICATIONS

KR Office Action for Appl. No. 10-2018-7028120, dated Jun. 15, 2023, 5 pages.
KR Preliminary Rejection for Appl. No. 10-2023-7017365, dated Jun. 15, 2023, 5 pages.
Notice of Allowance for U.S. Appl. No. 16/370,465 dated Jul. 12, 2023, 3 pages.
Non-Final Rejection for U.S. Appl. No. 16/773,740 dated Jun. 8, 2023, 8 pages.
Decision of Patent Grant for Appl. No. 10-2023-7017365, dated Oct. 4, 2023, 1 pages.
Notice of Allowance for U.S. Appl. No. 16/370,465 dated Apr. 7, 2023, 8 pages.
Notice of Allowance for U.S. Appl. No. 16/370,465, dated Mar. 7, 2023, 3 pages.
JP Office Action for Appl. No. 2020-531934, dated Jan. 10, 2023, 8 pages.
Notice of Preliminary Rejection for Appl. No. 1020187028120, dated May 18, 2022, 5 pages.
Office Action and Search Report for Appl. No. 20180044521.3, dated Jul. 1, 2022, 12 pages.
Office action for U.S. Appl. No. 16/370,465, dated Dec. 16, 2020, 9 pages.
Office action for U.S. Appl. No. 16/370,465, dated Jul. 2, 2021, 17 pages.
Oh et al., dated May 2005, P5-75, Novel robotic catheter remote control system: safety and accuracy in delivering RF Lesions in all 4 cardiac chambers, Heart Rhythm, 2(5):S277-S278.
Point Cloud, Sep. 10, 2010, Wikipedia, 2 pp.
Racadio et al., Dec. 2007, Live 3D guidance in the interventionail radiology suite, AJR, 189:W357-W364, 8 pages.
Reddy et al., May 2005, P1-53. Porcine pulmonary vein ablation using a novel robotic catheter control system and real-time integration of CT imaging with electroanatomical mapping, Hearth Rhythm, 2(5):S121, 1 page.
Sato et al., 2016, Techniques of stapler-based navigational thoracoscopic segmentectomy using virtual assisted lung mapping (VAL-MAP), Journal ofThoracic Disease, 8(Suppl 9):S716.
Shen et al., 2015, Robust camera localisation with depth reconstruction for bronchoscopic navigation. International Journal of Computer Assisted Radiology and Surgery, 10(6):801-813, 13 pages.
Shi et al., Sep. 14-18, 2014, Simultaneous catheter and environment modeling for trans-catheter aortic valve implantation, IEEE/RSJ International Conference on Intelligent Robots and Systems, pp. 2024-2202.
Slepian, dated 2010, Robotic Catheter Intervention: the Hansen Medical Sensei Robot Catheter System, PowerPoint presentation, 28 pages.
Solheim et ai., May 14, 2009, Navigated resection of giant intracranial meningiomas based on intraoperative 30 ultrasound, Acta Neurochir, 151:1143-1151.
Solomon et al., Dec. 2000, Three-dimensional CT-Guided Bronchoscopy With a Real-Time Electromagnetic Position Sensor A Comparison of Two Image Registration Methods, Chest, 118(6):1783-1787.

Song et al., 2012, Autonomous and stable tracking of endoscope instrument tools with monocular camera, Advanced Intelligent Mechatronics (AIM), 2012 IEEE-ASME International Conference on.IEEE, 6 pages.
Vemuri et al., Dec. 2015, Inter-operative biopsy site relocations in endoluminal surgery, IEEE Transactions on Biomedical Engineering, Institute of Electrical and Electronics Engineers, < 10 .1109/ T8ME 2015.2503981 >, 13 pages.
Verdaasdonk et al., Jan. 23, 2012, Effect of Microsecond Pulse Length and Tip Shape on Explosive Bubble Formation of 2.78 μm Er,Cr;YSGG and 2.94 um Er:YAG laser, Proceedings of SPIE, vol. 8221, 12, 1 pages.
Wilson et al., 2008, A Buyer's Guide to Electromagnetic Tracking Systems for Clinical Applications, Proc. of SPCI, 6918:691828-1, 12 pages.
Yip et al., 2012, Tissue tracking and registration for image-guided surgery, IEEE transactions on medical imaging 31 (11 ):2169-2182, 14 pages.
Zhou et al., 2010, Synthesis of stereoscopic views from monocular endoscopic videos, Compute Vision and Pattern Recognition Workshops (CVPRVV), 2010 IEEE Computer Society Conference on IEE, 8 pages.
Notice of Acceptance for Appl. No. 2018384820, dated Jun. 20, 2024, 3 pages.
Non-Final Rejection for U.S. Appl. No. 16/773,740, dated Apr. 26, 2024, 11 pages.
AU Examination Report for Appl. No. 2018384820, dated Jan. 12, 2024, 5 pages.
KR Preliminary Rejection for Appl. No. 10-2020-7013659, dated Nov. 17, 2023, 11 pages.
Notice of Acceptance for Appl. No. 2017388217, dated Oct. 17, 2022, 3 pages.
Notice of Allowance for U.S. Appl. No. 16/370,465, dated Dec. 23, 2022, 9 pages.
Al-Ahmad et al., dated 2005, Early experience with a computerized robotically controlled catheter system, Journal of Interventional Cardiac Electrophysiology, 12:199-202, 4 pages.
AU Examination Report for Appl. No. 2017388217, dated Jul. 19, 2022, 3 pages.
Blankenstein, Jun. 2008, Dynamic Registration and High Speed Visual Servoing in Robot-Assisted Surgery, Katholieke Universiteit Leuven, Leuven, Belgium, 96 pages.
Ciuti et al., 2012, Intra-Operative Monocular 3D Reconstruction for Image-Guided Navigation in Active Locomotion Capsule Endoscopy. Biomedical Robotics And Biomechatronics (Biorob), 4th IEEE Ras & Embs International Conference On IEEE, 7 pages.
CN 3rd Office Action for appl No. 201780021723, dated Aug. 31, 2021, 4 pages.
CN office action for Appl. No. 201780021756.1, dated Mar. 1, 2021, 7 pages.
EP search report for U.S. Appl. No. 18/889,789, dated Jun. 1, 2021, 2 pages.
EP written opinion for U.S. Appl. No. 18/889,789, dated Jun. 1, 2021, 4 pages.
Fallavoliita et al., 2010, Acquiring Multiview C-Arm Images to Assist Cardiac Ablation Procedures, EURASIP Joumal on Image and Video Processing, vol. 2010, Article ID 871408, pp. 1-10.
Final Rejection for U.S. Appl. No. 16/219,766, dated Dec. 22, 2021, 6 pages.
Final Rejection for U.S. Appl. No. 16/219,766, dated Nov. 8, 2019, 8 pages.
Final Rejection for U.S. Appl. No. 16/370,465, dated Jul. 2, 2021, 17 pages.
Final Rejection for U.S. Appl. No. 16/773,740, dated Oct. 24, 2022, 8 pages.
Gutierrez et al., Mar. 2008, A Practical Global Distortion Correction Method for an Image Intensifier Based X-Ray Fluoroscopy System, Med. Phys, 35(3):997-1007, 11 pages.
Haigron et al., 2004, Depth-map-based scene analysis for active navigation in virtual angioscopy, IEEE Transactions on Medical Imaging, 23( 11 ): 1380-1390, 11 pages.

(56) References Cited

OTHER PUBLICATIONS

Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).

Hansen Medical, Inc. Bibliography, product brochure, 1 p., dated as available athttp://hansenmedical.com/bibliography.aspx on Jul. 14, 2006 (accessed Jun. 25, 2019 using the internet archive way back machine).

Hansen Medical, Inc. dated 2007, Introducing the Sensei Robotic Catheter System, product brochure, 10 pages.

Hansen Medical, Inc. dated 2009, Sensei X Robotic Catheter System, product brochure, 3 pp.

Jansen Medical, Inc. Technology Advantages, product brochure, 1 p., dated as available at http://hansenmedical.com/advantages aspx on Jul. 13, 2006 (accessed Jun. 25, 2019 using the internet archive way back machine).

International Search Report and Written Opinion dated Feb. 26, 2019 in application No. PCT/US2018/065530, 13 bages.

International Search Report and Written Opinion in application No. PCT/US2017/068535, dated Jul. 5, 2018.

International Search Report and Written Opinion in application No. PCT/US2017/068535, dated May 18, 2018, 15 bages.

JP Office Action for appl No. 2019534667, dated Oct. 19, 2021, 7 pages.

JP Office Action for Appl. No. 2019534667, dated Sep. 13, 2022, 2 pages.

Kiraly et al., 2002, Three-dimensional Human Airway Segmentation Methods for Clinical Virtual Bronchoscopy, Acad Radio!, 9:1153-1168, 16 pages.

Kiraly et al., Sep. 2004, Three-dimensional path planning for virtual bronchoscopy, IEEE Transactions on Medical Imaging, 23(9):1365-1379, 15 pages.

Konen et al., 1998, The VN-project endoscopic image processing for neurosurgery, Computer Aided Surgery, 3:1-6 , 6 pages.

KR Final Rejection for Appl. No. 1020187028120, dated Nov. 3, 2022, 3 pages.

Kukuk, Oct. 5, 2001, TBNA-protocols: Guiding TransBronchial Needle Aspirations Without a Computer in the Operating Room, MICCAI 2001, 2208:997-1006.

Kumar et al., 2014, Stereoscopic visualization of laparoscope image using depth information from 3D model, Computer methods and programs in biomedicine 113(3):862-868, 7 pages.

Lawton et al., 1999, Ribbons and groups: A thin rod theory for catheters and filaments, J. Phys. A., 1999, 32:1709-1735, 27 pages.

Livatino et al., 2015, Stereoscopic visualization and 3-D technologies in medical endoscopic teleoperation, IEEE, 11 pages.

Luo et al., 2010, Modified hybrid bronchoscope tracking based on sequential monte carlo sampler: Dynamic phantom validation, Asian Conference on Computer Vision. Springer, Berlin, Heidelberg, 13 pages.

Marrouche et al., dated May 6, 2005, AB32-1, Preliminary human experience using a novel robotic catheter remote control, Heart Rhythm, 2(5):S63, 1 page.

Mayo Clinic, Robotic Surgery, https://www.mayoclinic.org/tests-procedures/robotic-surgery/about/pac- 20394974?p=1, downloaded from the internet on Jul. 12, 2018, 2 pgs.

Mourgues et al., 2002, Flexible calibration of actuated stereoscopic endoscope for overlay in robot 672 assisted surgery, International Conference on Medical Image Computing and Computer-Assisted Intervention. SprinQer, Berlin, HeidelberQ, 10 pages.

Nadeem et al., 2016, Depth Reconstruction and Computer-Aided Polyp Detection in Optical Colonoscopy Video Frames, arXiv preprint arXiv:1609.01329, 12 pages.

Non Final Rejection for U.S. Appl. No. 16/219,766, dated Apr. 30, 2019, 6 pages.

Non Final Rejection for U.S. Appl. No. 16/219,766, dated Oct. 23, 2020, 7 pages.

Non Final Rejection for U.S. Appl. No. 16/219,766, dated Sep. 8, 2021, 9 pages.

Non Final Rejection for U.S. Appl. No. 16/370,465, dated Dec. 16, 2020, 9 pages.

Non-Final Rejection for U.S. Appl. No. 16/773,740, dated Jun. 14, 2022, 9 pages.

Notice of Allowance for U.S. Appl. No. 16/219,766, dated Mar. 16, 2022, 7 pages.

Notice of Allowance for U.S. Appl. No. 16/219,766, dated Mar. 19, 2021, 7 pages.

Notice of Allowance for U.S. Appl. No. 16/370,465, dated Feb. 11, 2022, 6 pages.

Notice of allowance for appl No. 1637465, dated Oct. 20, 2021, 10 pages.

Notice of Allowance for U.S. Appl. No. 16/219,766, dated Jul. 11, 2022, 9 pages.

Notice of Allowance for U.S. Appl. No. 16/370,465, dated Aug. 29, 2022, 6 pages.

Notice of Allowance for U.S. Appl. No. 16/370,465, dated May 19, 2022, 8 pages.

Notice of Allowance for U.S. Appl. No. 16/370,465, dated Jan. 24, 2023, 3 pages.

JP Office Action for Appl. No. 2023-061290, dated Jul. 26, 2023, 5 pages.

CN 2nd Office Action for Appl. No. 201880044521.3, dated Mar. 14, 2023, 4 pages.

EP Examination Report for Appl. No. 17835908.9, dated Nov. 3, 2023, 7 pages.

Final Rejection for U.S. Appl. No. 16/773,740, dated Dec. 18, 2023, 9 pages.

Office Action from Japan Patent Application No. 2019-534667, dated Oct. 19, 2021, 1 pages.

Non-Final Office Action from U.S. Appl. No. 15/392,917, dated Nov. 3, 2017, 14 pages.

Final Office Action from U.S. Appl. No. 15/392,917, dated Mar. 19, 2018, 13 pages.

Non-Final Office Action from U.S. Appl. No. 15/392,868, dated Jul. 20, 2018, 10 pages.

Final Office Action from U.S. Appl. No. 15/392,868, dated Jan. 4, 2019, 12 pages.

Non-Final Office Action from U.S. Appl. No. 15/392,868, dated May 30, 2019, 8 pages.

Notice of Allowance from U.S. Appl. No. 15/392,868, dated Sep. 13, 2019, 8 pages.

Final Office Action from U.S. Appl. No. 16/773,740, dated Oct. 31, 2024, 11 pages.

* cited by examiner

MULTIPLE-INPUT INSTRUMENT POSITION DETERMINATION

CROSS-REFERENCE TO RELATED APPLICATIONS

This application is a continuation of U.S. patent application Ser. No. 16/219,766, filed Dec. 13, 2018, now U.S. Pat. No. 11,510,736, which claims the benefit of U.S. Provisional Application No. 62/598,934, filed Dec. 14, 2017, the disclosures of which are hereby incorporated by reference in their entireties.

TECHNICAL FIELD

This application relates generally to estimating a location of an instrument, and more particularly to systems and methods for estimating a location of a robotically-enabled medical instrument based on a comparison of location input data.

BACKGROUND

Medical procedures such as endoscopy may involve accessing and visualizing the inside of a patient's luminal network for diagnostic and/or therapeutic purposes. For example, bronchoscopy is a medical procedure that allows a physician to examine airways, such as bronchi and bronchioles, in a patient's lungs. During the procedure, a thin, flexible instrument, known as a bronchoscope, may be inserted into the patient's mouth and passed down the patient's throat into the lung. The instrument is navigated through the lung's airways towards a tissue site identified for subsequent diagnosis and/or treatment.

In certain procedures, a robotically-enabled medical system may be used to control the insertion and/or manipulation of the instrument. The robotically-enabled medical system may include a robotic arm, or other instrument positioning device, having a manipulator assembly used to control the positioning of the instrument during the procedure.

SUMMARY

In a first aspect, a non-transitory computer readable storage medium having stored thereon instructions is described. The instructions, when executed, cause a processor of a device to at least: obtain a first motion estimate for an instrument based on robotic data regarding physical manipulation of the instrument; obtain a second motion estimate for the instrument based on position sensor data received from at least one position sensor; determine a motion estimate disparity based on a comparison of the first motion estimate and the second motion estimate; based on the motion estimate disparity, update (a) a weighting factor for a location derivable from the robotic data, or (b) a weighting factor for a location derivable from the position sensor data; and determine a location/position estimate for the instrument based on the updated weighting factor.

The non-transitory computer readable storage medium can include one or more of the following features, in any combination: (a) wherein the instructions, when executed, cause the processor to: decrease the weighting factor for a location derivable from the robotic data, or increase the weighting factor for a location derivable from the position sensor data, when the motion estimate disparity indicates that the second motion estimate exceeds the first motion estimate; (b) wherein the instructions, when executed, cause the processor to determine that the instrument has experienced a hysteresis condition when the motion estimate disparity indicates that the second motion estimate exceeds the first motion estimate; (c) wherein the instructions, when executed, cause the processor to: decrease the weighting factor for a location derivable from the robotic data, or increase the weighting factor for a location derivable from the position sensor data, when the motion estimate disparity indicates that the first motion estimate exceeds the second motion estimate; (d) wherein the instructions, when executed, cause the processor to determine that the instrument has experienced a buckling condition when the motion estimate disparity indicates that the first motion estimate exceeds the second estimate; (e) wherein the instructions, when executed, cause the processor to update the weighting factor for a location derivable from the robotic data to zero; (f) wherein the instructions, when executed, cause the processor to determine the motion estimate disparity by determining a difference between the first motion estimate and the second motion estimate; (g) wherein the instructions, when executed, cause the processor to update: the weighting factor for a location derivable from the robotic data, or the weighting factor for a location derivable from the position sensor data, when the difference exceeds a disparity threshold value; (h) wherein the instructions, when executed, cause the processor to: obtain the first motion estimate by determining a change in position of the instrument based on the robotic data during an interval, and obtain the second motion estimate by determining a change in position of the instrument based on the position sensor data during the interval; (i) wherein the interval is a time interval; (j) wherein the interval is a distance interval; (k) wherein the position estimate is determined based on the updated weighting factor, the location derivable from the robotic data, and the location derivable from the position sensor data; (l) wherein the position sensor is positioned on the instrument; (m) wherein the position sensor comprises an EM sensor; (n) wherein the position sensor comprises an imaging device positioned on the instrument, and wherein the processor is further configured to determine positional information from images captured by the imaging device; (o) wherein the at least one position sensor comprises at least one of: a shape-sensing fiber, an accelerometer, a gyroscope, an electromagnetic sensor, an imaging device, and an ultrasonic sensor; (p) wherein the instruction, when executed, are cause the processor to: obtain a third motion estimate for the instrument based on vision data received from an imaging device positioned on the instrument, determine the motion estimate disparity based on a comparison of the second motion estimate and the third motion estimate, and based on the motion estimate disparity, update a weighting factor for a location derivable from the vision data; (q) wherein the instructions, when executed, cause the processor to: increase the weighting factor for a location derivable from the position sensor data, or decrease the weighting factor for a location derivable from the vision, when the motion estimate disparity indicates that the second motion estimate exceeds the third motion estimate; (r) wherein the instructions, when executed, cause the processor to determine that the instrument has experienced a hysteresis condition when the motion estimate disparity indicates that the second motion estimate exceeds the third motion estimate; (s) wherein the instructions, when executed, cause the processor to: increase the weighting factor for a location derivable from the position sensor data, or decrease the weighting factor for a location derivable from the vision data, when the motion estimate disparity indicates that the third motion estimate exceeds the second motion estimate; and/or (t) wherein the instructions, when executed, cause the processor to determine that the instrument has experienced a buckling condition when the motion estimate disparity indicates that the third motion estimate exceeds the second estimate.

In another aspect, a robotic system is described. The robotic system includes an instrument having an elongate body and at least one position sensor disposed on the elongate body; an instrument positioning device attached to the instrument and configured to move the instrument; at least one computer-readable memory having stored thereon executable instructions; and one or more processors in communication with the at least one computer-readable memory and configured to execute the instructions to cause the system to at least: obtain a first motion estimate for the instrument based on robotic data regarding physical manipulation of the instrument with the instrument positioning device; obtain a second motion estimate for the instrument based on position sensor data received from at least one position sensor; determine a motion estimate disparity based on a comparison of the first motion estimate and the second motion estimate; based on the motion estimate disparity, update: a weighting factor for a location derivable from the robotic data, or a weighting factor for a location derivable from the position sensor data; and determine a location/position estimate for the instrument based on the updated weighting factor.

The system may include one or more of the following features in any combination: (a) wherein the instrument comprises an endoscope; (b) wherein the instrument positioning device comprises a robotic arm; (c) wherein the at least one position sensor comprises an EM sensor; (d) wherein the at least one position sensor comprises an imaging device positioned on the instrument, and wherein the instructions further cause the one or more processors to determine positional information from images captured by the imaging device; (e) wherein the at least one position sensor comprises a shape-sensing fiber, an accelerometer, a gyroscope, an electromagnetic sensor, an imaging device, or an ultrasonic sensor; (f) wherein the instructions, when executed cause the one or more processors to: decrease the weighting factor for the location derivable from the robotic data, or increase the weighting factor for the location derivable from the position sensor data, when the motion estimate disparity indicates that the second motion estimate exceeds the first motion estimate; (f) wherein the instructions, when executed cause the one or more processors to determine that the instrument has experienced a hysteresis condition when the motion estimate disparity indicates that the second motion estimate exceeds the first motion estimate; (g) wherein the instructions, when executed cause the one or more processors to: decrease the weighting factor for the location derivable from the robotic data, or increase the weighting factor for the location derivable from the position sensor data, when the motion estimate disparity indicates that the first motion estimate exceeds the second motion estimate; (h) wherein the instructions, when executed cause the one or more processors to determine that the instrument has experienced a buckling condition when the motion estimate disparity indicates that the first motion estimate exceeds the second motion estimate; (i) wherein the instructions, when executed cause the one or more processors to update the weighting factor for the location derivable from the robotic data to zero when the motion estimate disparity indicates that the second motion estimate exceeds the first motion estimate; (j) wherein the instructions, when executed cause the one or more processors to update the weighting factor for the location derivable from the position sensor data to zero when the motion estimate disparity indicates that the first motion estimate exceeds the second motion estimate; (k) when executed cause the one or more processors to determine the motion estimate disparity by determining a difference between the first motion estimate and the second motion estimate; (l) wherein the instructions, when executed cause the one or more processors to update: the weighting factor for the location derivable from the robotic data, or the weighting factor for the location derivable from the position sensor data, when the difference exceeds a disparity threshold value; (m) wherein the instructions, when executed cause the one or more processors to: obtain the first motion estimate by determining a change in position of the instrument based on the robotic data during an interval, and obtain the second motion estimate by determining a change in position of the instrument based on the position sensor data during the interval; (n) wherein the interval is a time interval; and/or (o) wherein the interval is a distance interval.

In another aspect, a method for navigating an instrument within an interior region of a body is described. The method includes: obtaining a first motion estimate for an instrument based on robotic data regarding physical manipulation of the instrument; obtaining a second motion estimate for the instrument based on position sensor data received from at least one position sensor; determining a motion estimate disparity based on a comparison of the first motion estimate and the second motion estimate; based on the motion estimate disparity, updating: a weighting factor for a location derivable from the robotic data, or a weighting factor for a location derivable from the position sensor data; and determining a location/position estimate for the instrument based on the updated weighting factor.

The method may include one or more of the following features, in any combination: (a) wherein updating the weighting factor comprises decreasing the weighting factor for the location derivable from the robotic data, or increasing the weighting factor for the location derivable from the position sensor data, when the motion estimate disparity indicates that the second motion estimate exceeds the first motion estimate; (b) determining that the instrument has experienced a hysteresis condition when the motion estimate disparity indicates that the second motion estimate exceeds the first motion estimate; (c) wherein updating the weighting factor comprises decreasing the weighting factor for the location derivable from the robotic data, or increasing the weighting factor for the location derivable from the position sensor data, when the motion estimate disparity indicates that the first motion estimate exceeds the second motion estimate; (d) determining that the instrument has experienced a buckling condition when the motion estimate disparity indicates that the first motion estimate exceeds the second motion estimate; (e) updating the weighting factor for the location derivable from the robotic data to zero when the motion estimate disparity indicates that the second motion estimate exceeds the first motion estimate; (f) updating the weighting factor for the location derivable from the position sensor data to zero when the motion estimate disparity indicates that the first motion estimate exceeds the second motion estimate; (g) determining the motion estimate disparity comprises determining a difference between the first motion estimate and the second motion estimate; (h) determining the difference comprises determining a magnitude of the difference; (i) updating the weighting factor for the location derivable from the robotic data, or the weighting factor for the location derivable from the position sensor data, when the difference exceeds a disparity threshold value; (j) obtaining the first motion estimate comprises determining a change in position of the instrument based on the robotic data during an interval, and obtaining the second motion estimate comprises determining a change in position of the instrument based on the position sensor data during the interval; (k) wherein the interval is a time interval; (l) wherein the interval is a distance interval; (m) wherein the position sensor is positioned on the instrument; (n) wherein the position sensor comprises an EM sensor; (o) wherein the position sensor comprises an imaging device positioned on the instrument, and wherein the method further comprises determining positional information from images captured by the imaging device; and/or (p) wherein the position sensor comprises a shape-sensing fiber, an accelerometer, a gyroscope, an electromagnetic sensor, an imaging device, or an ultrasonic sensor.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
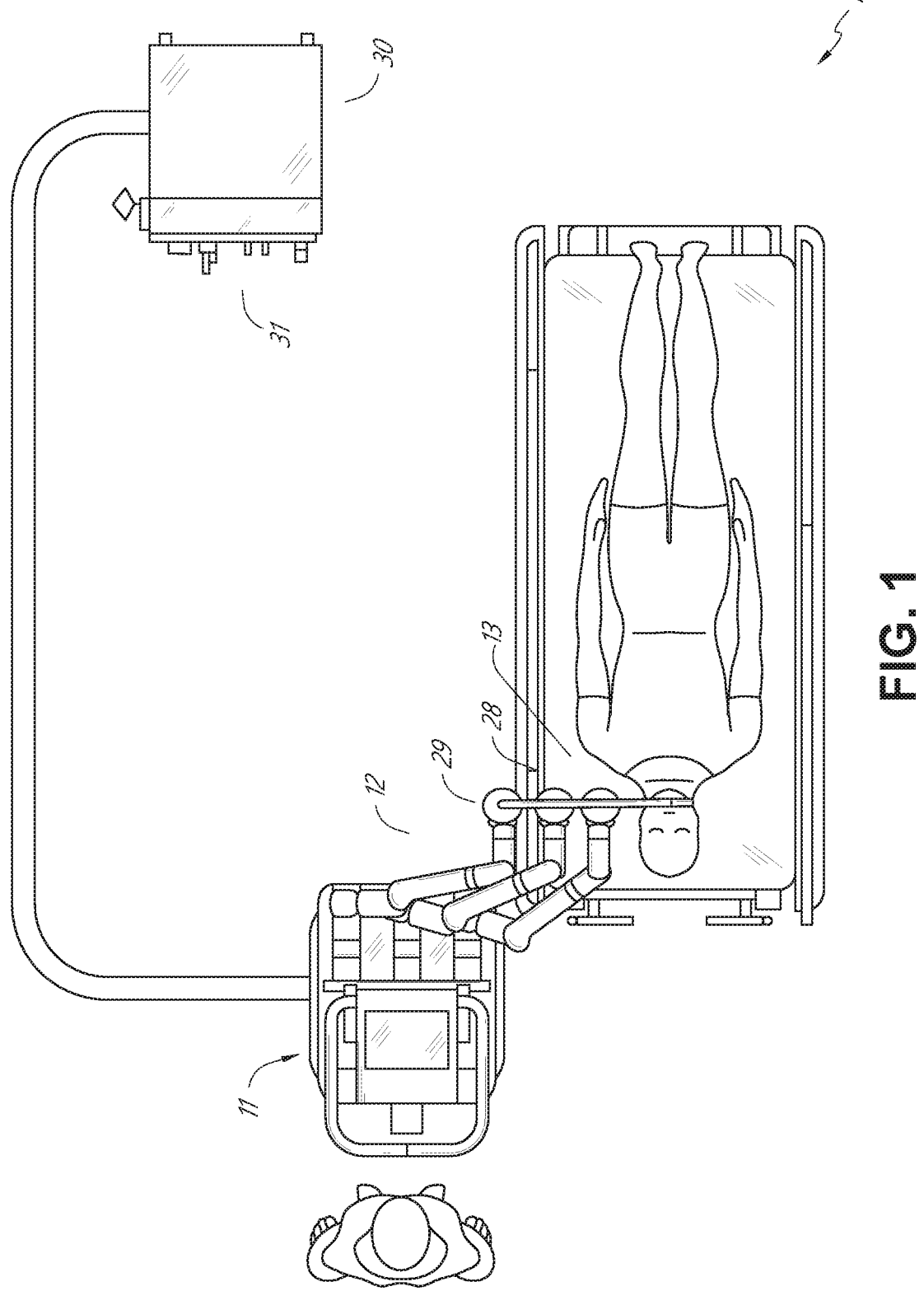
FIG. 1 illustrates an embodiment of a cart-based robotic system arranged for diagnostic and/or therapeutic bronchoscopy procedure(s).
Figure 2:
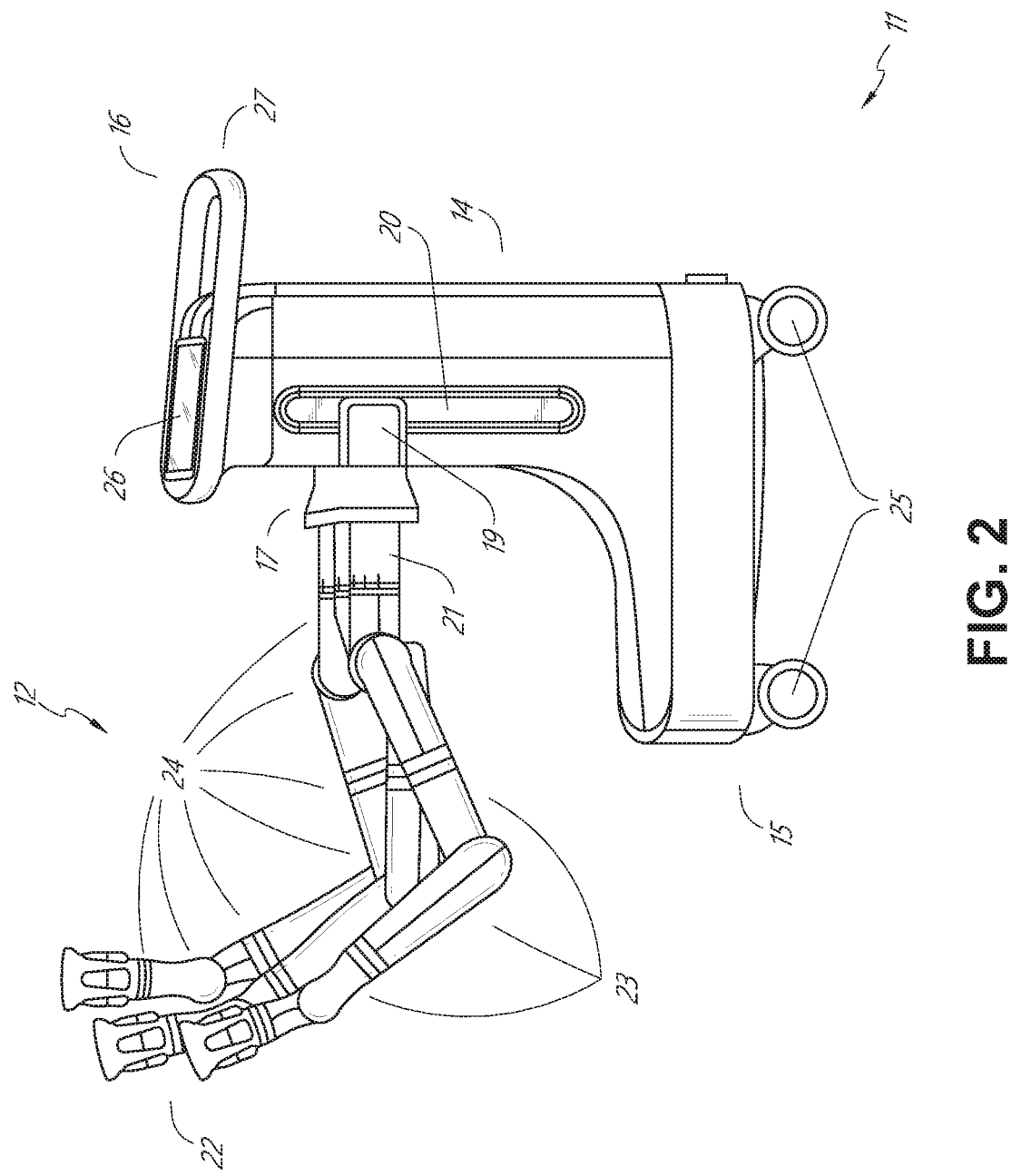
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician may view the console 16, robotic arms 12, and patient while operating the console 16 from behind the cart 11. As shown, the console 16 also includes a handle 27 to assist with maneuvering and stabilizing cart 11.

Figure 3:
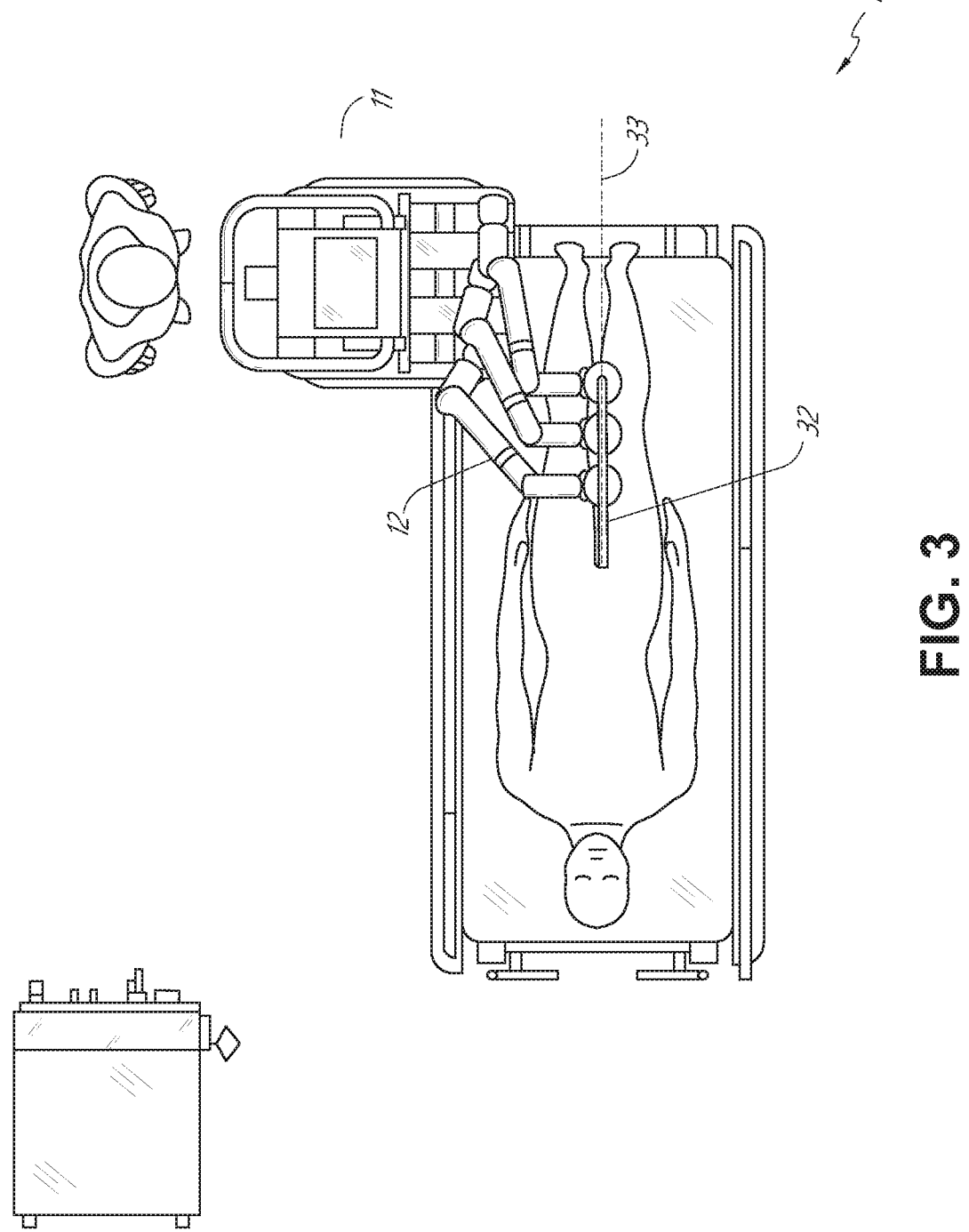
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
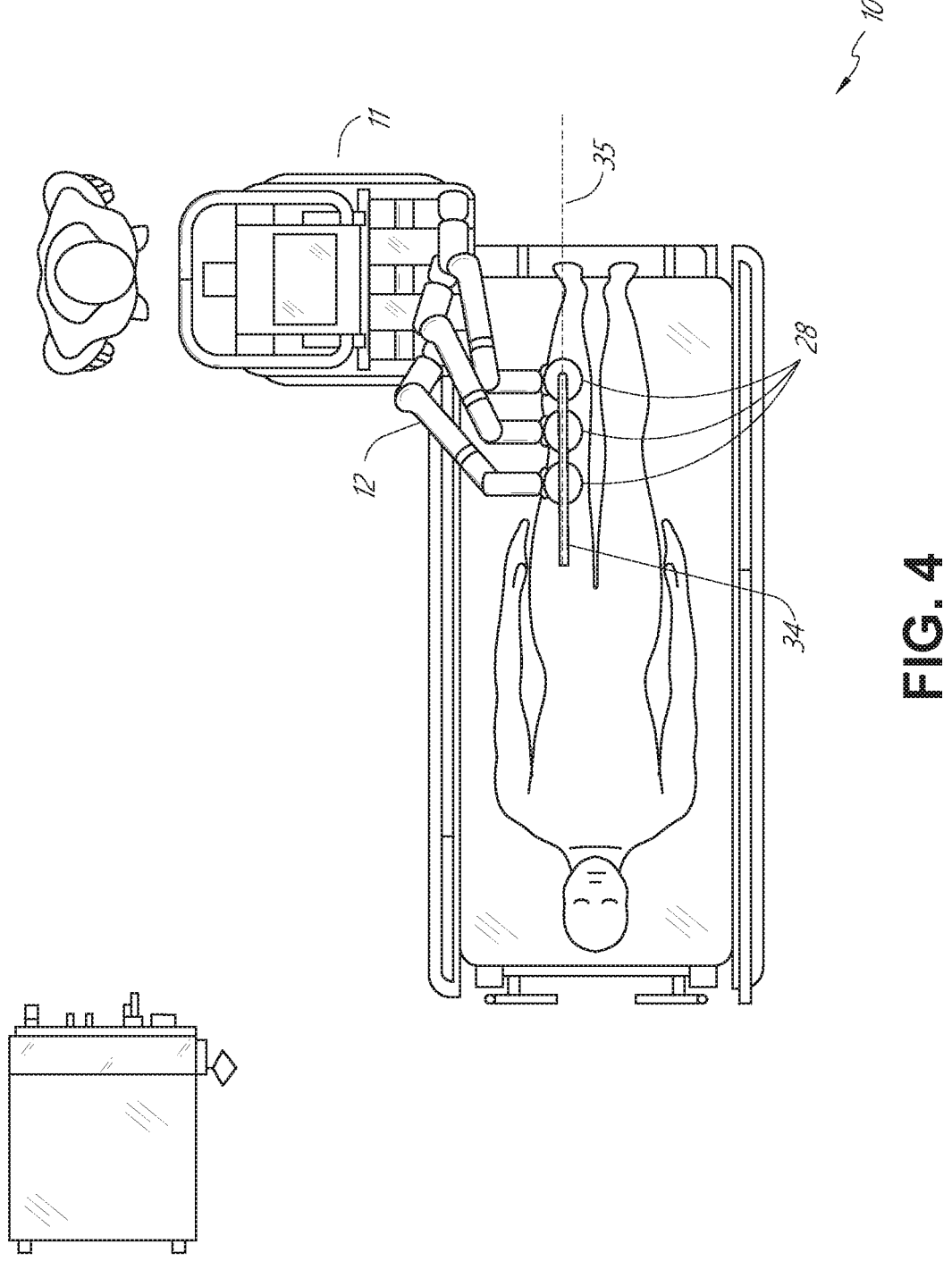
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
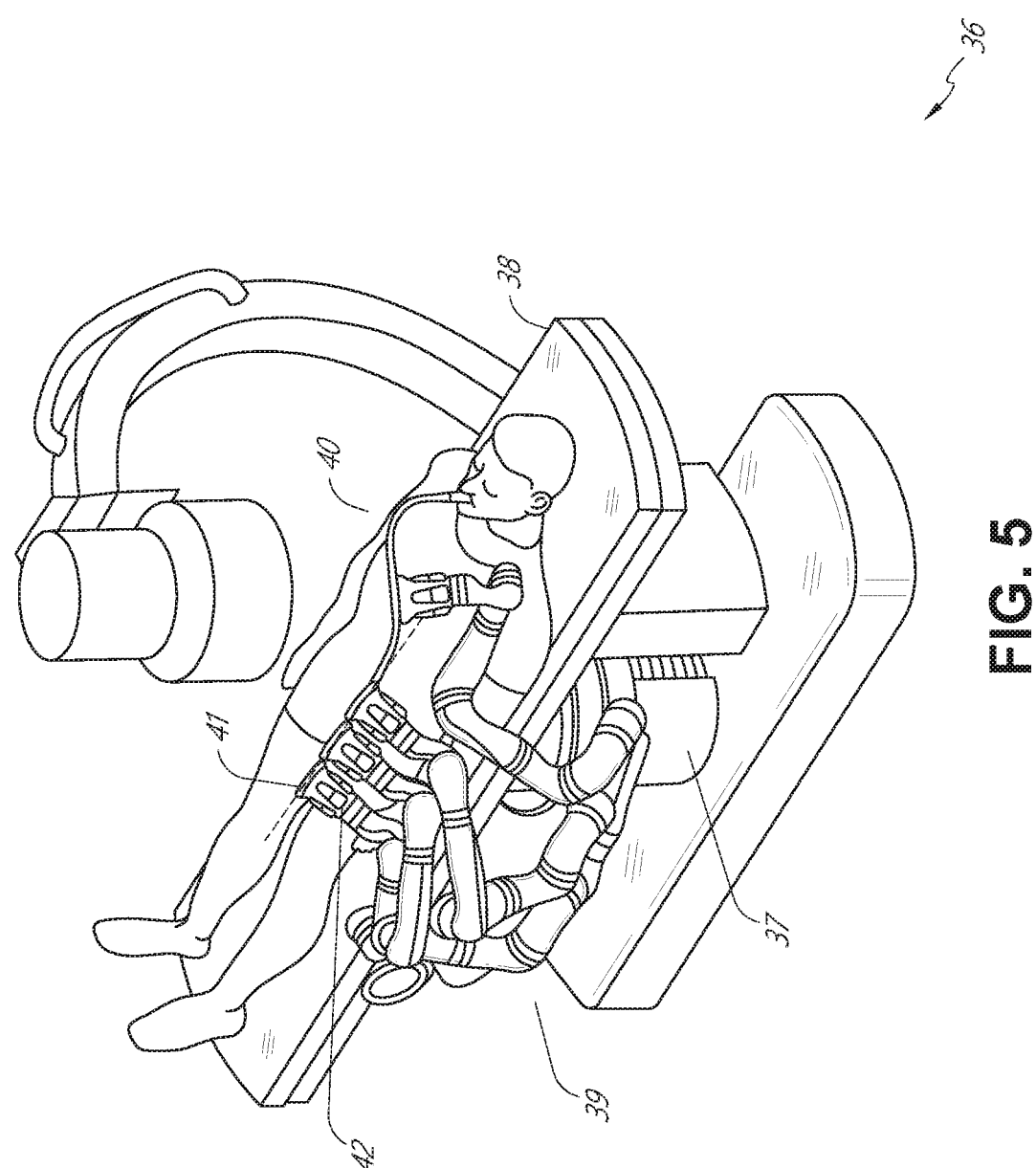
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
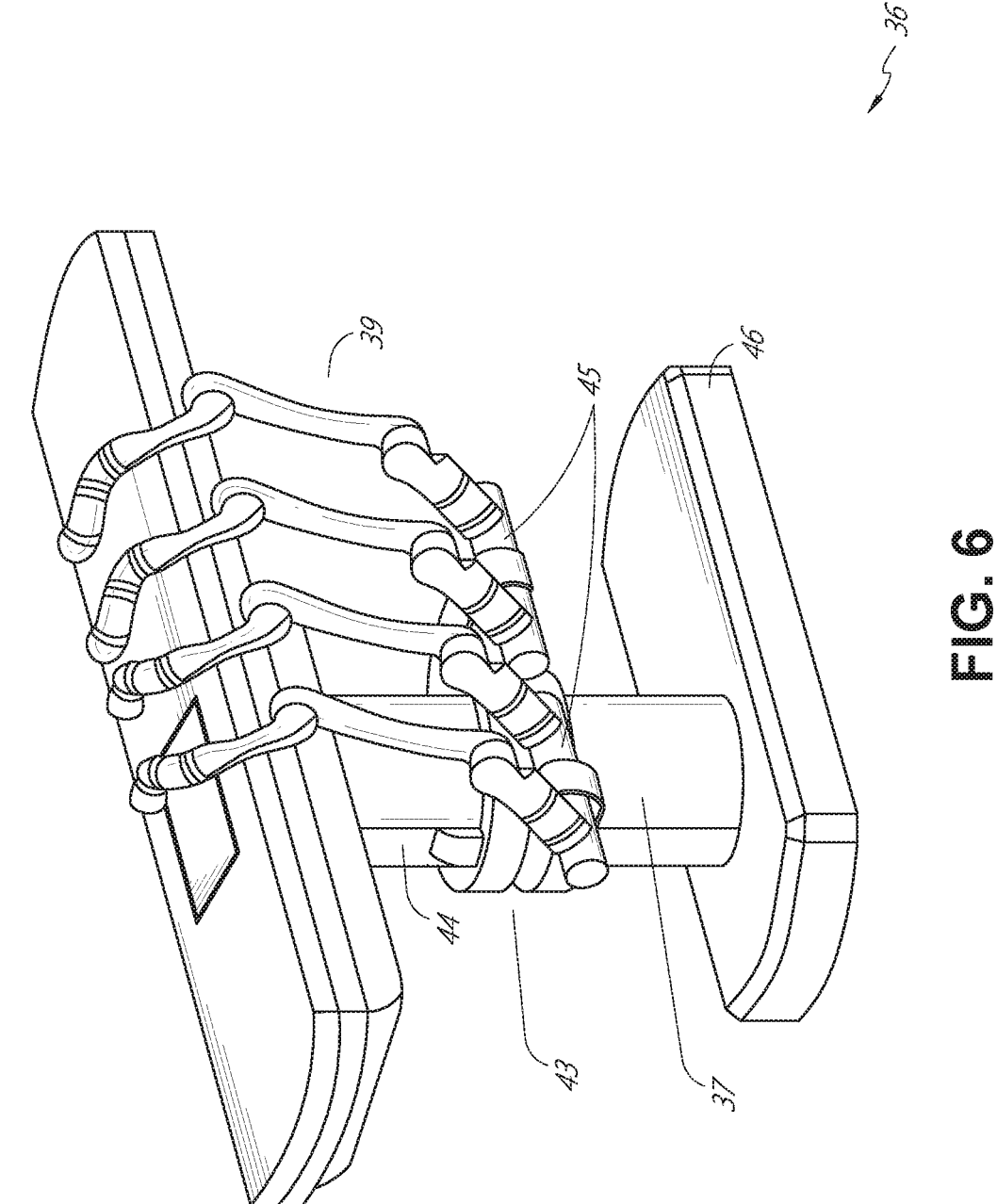
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
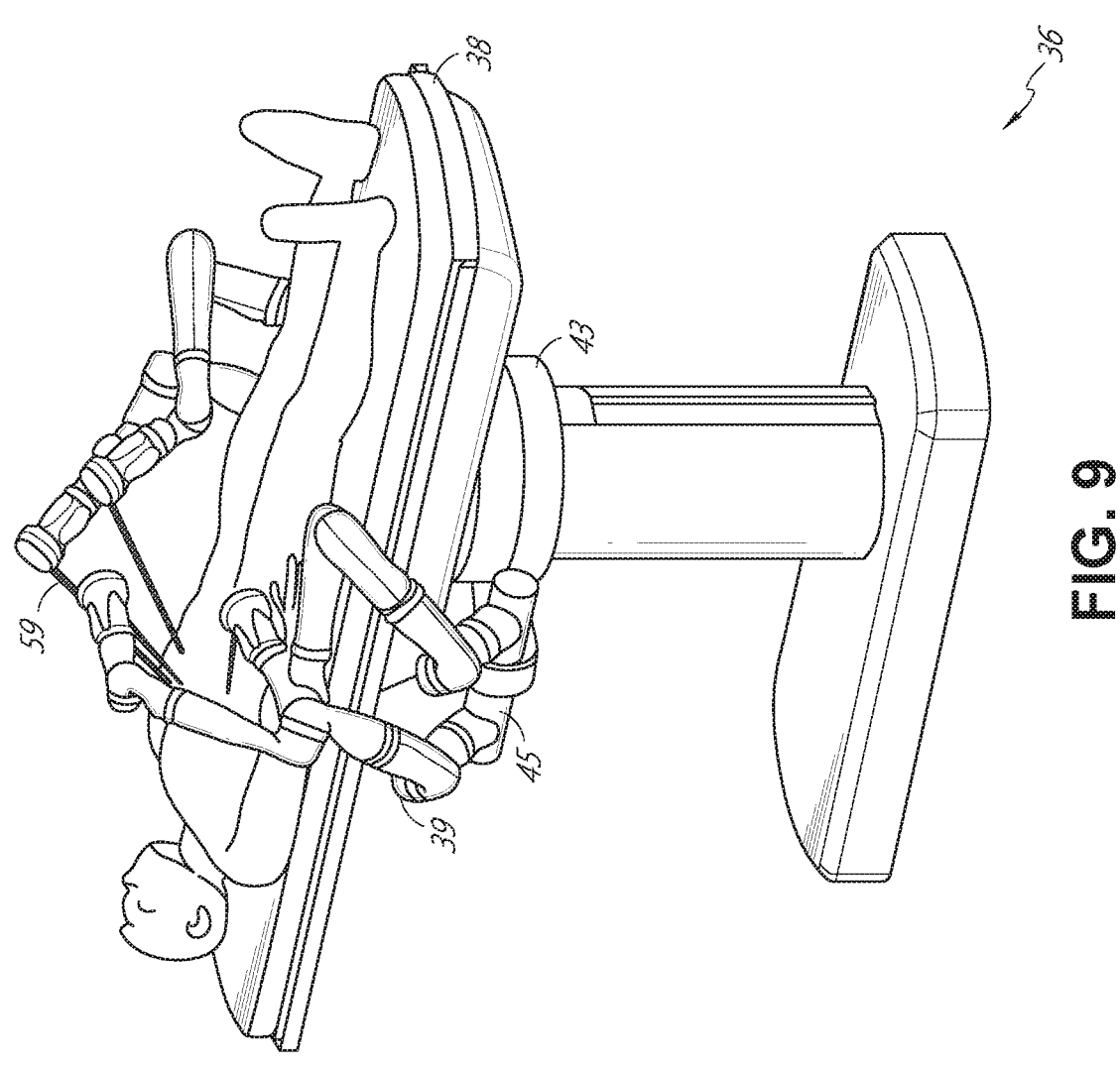
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
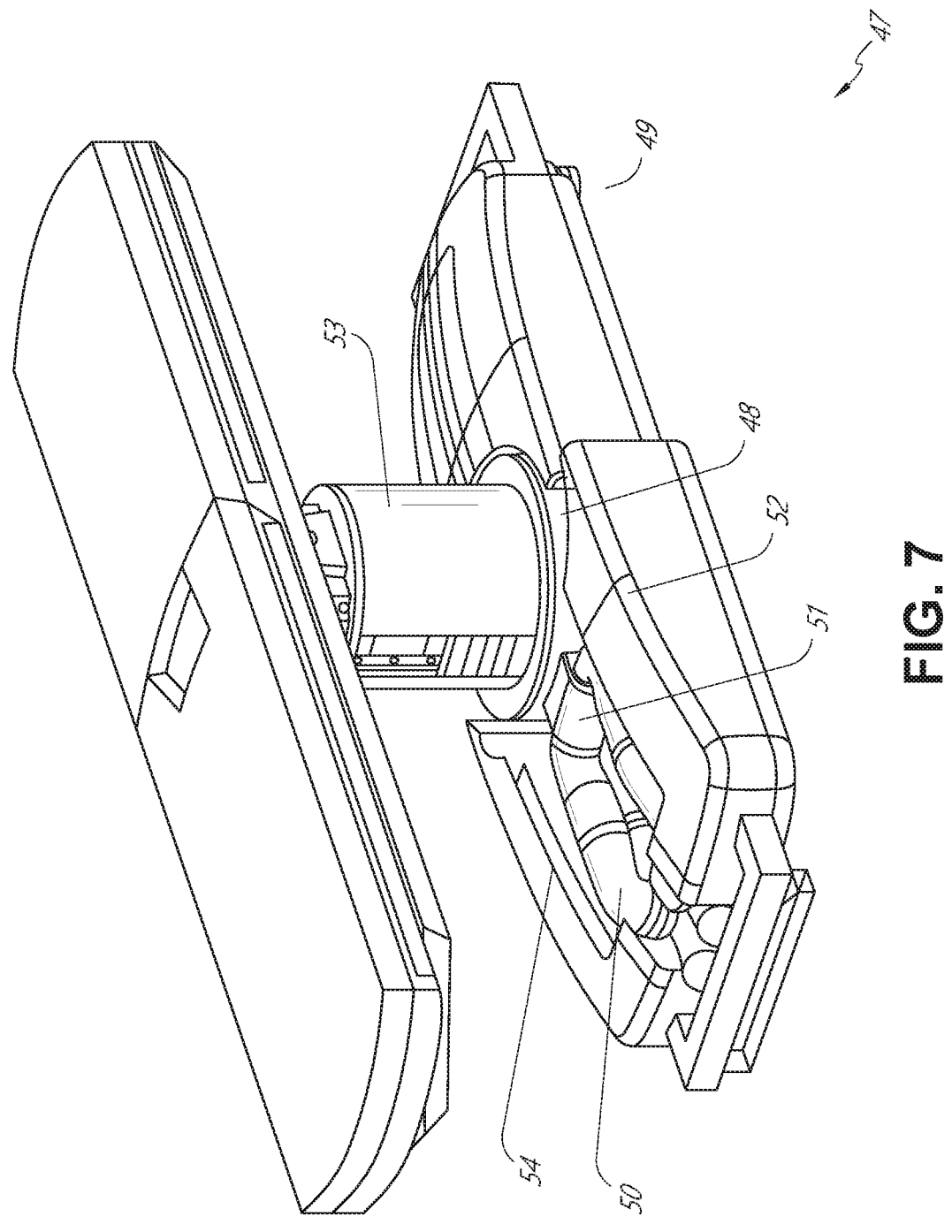
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
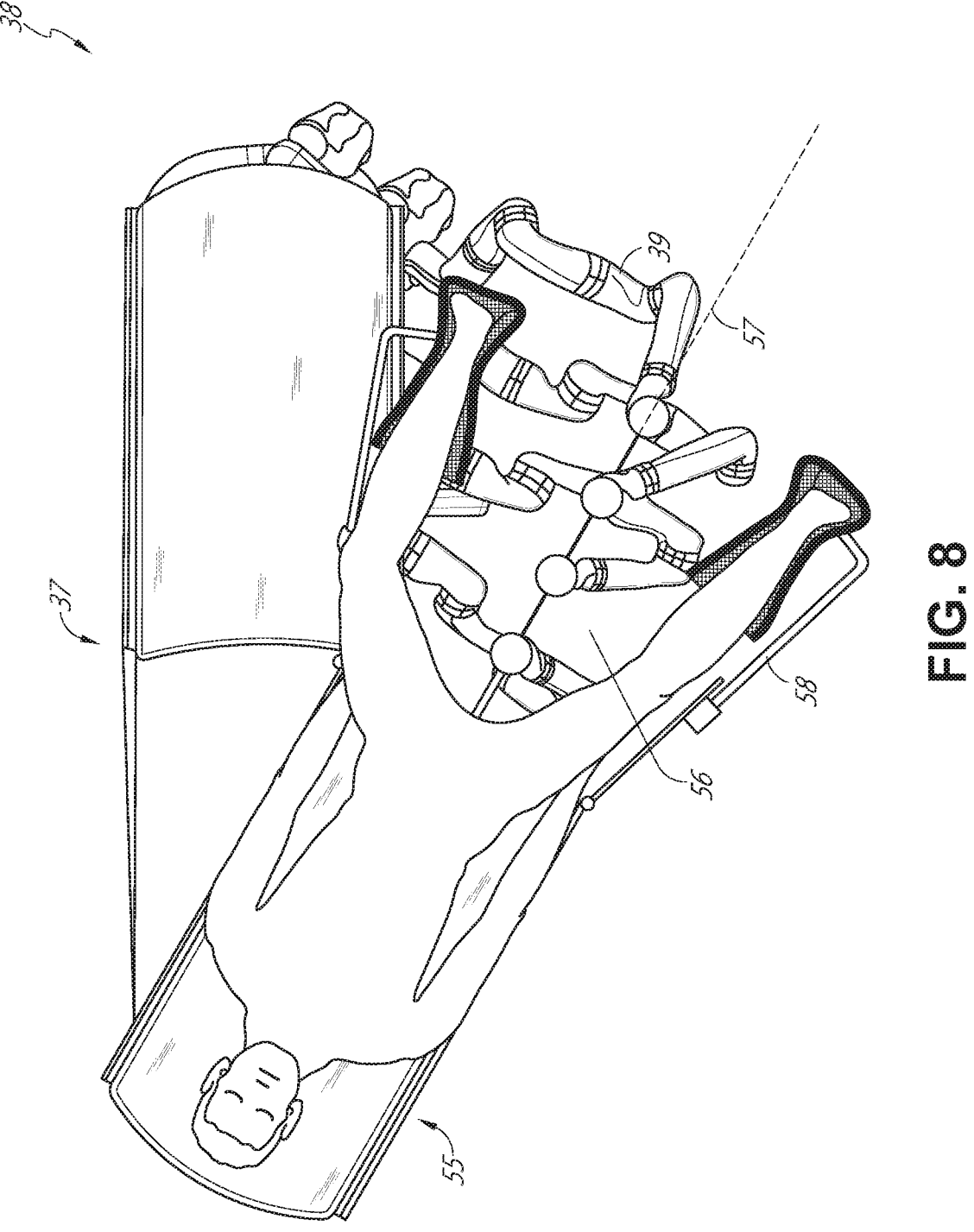
FIG. 8 illustrates an embodiment of a table-based robotic system configured for a ureteroscopy procedure.

FIG. 8 illustrates an embodiment of a robotically-enabled table-based system configured for a ureteroscopy procedure. In ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical or medical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
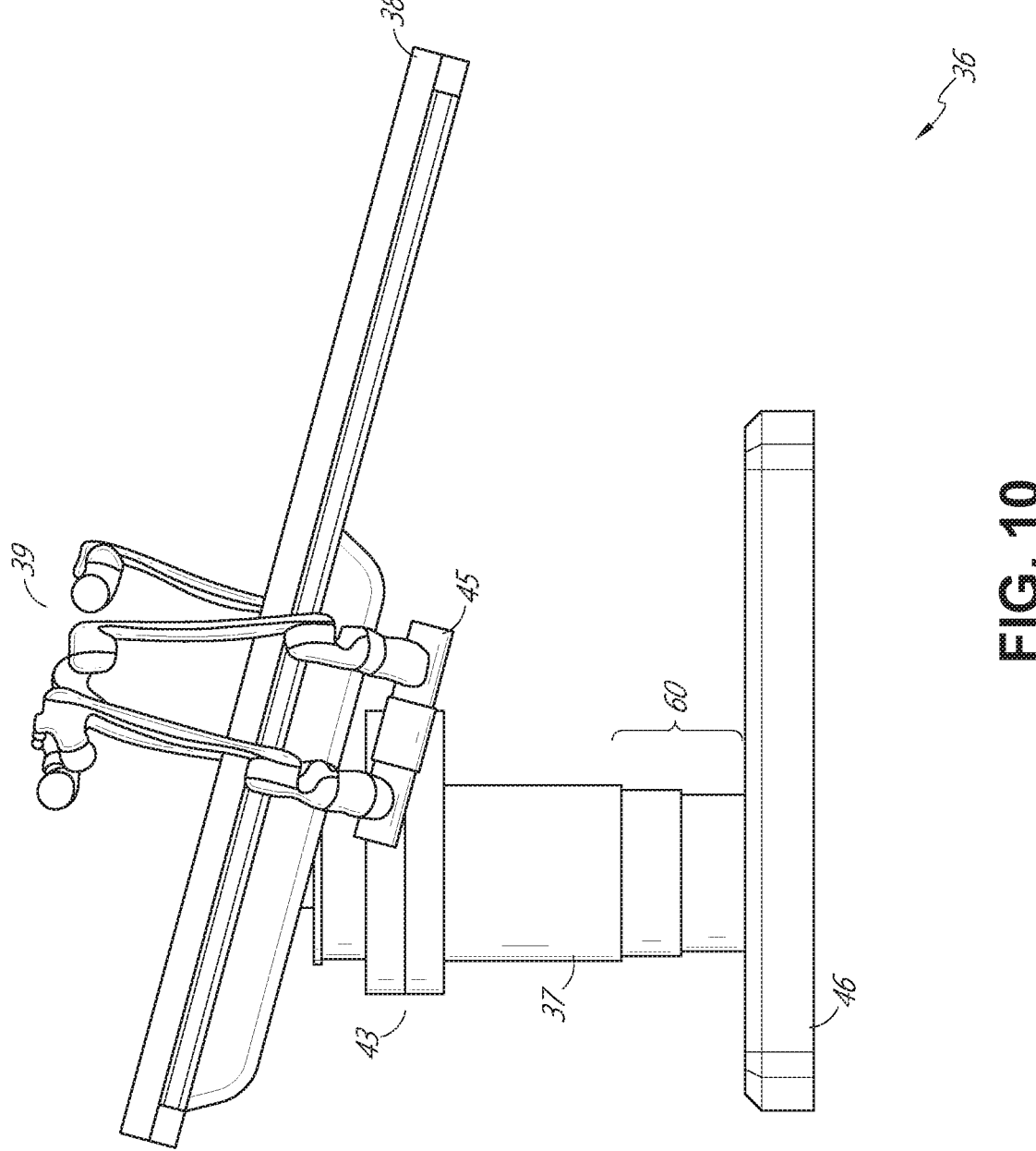
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
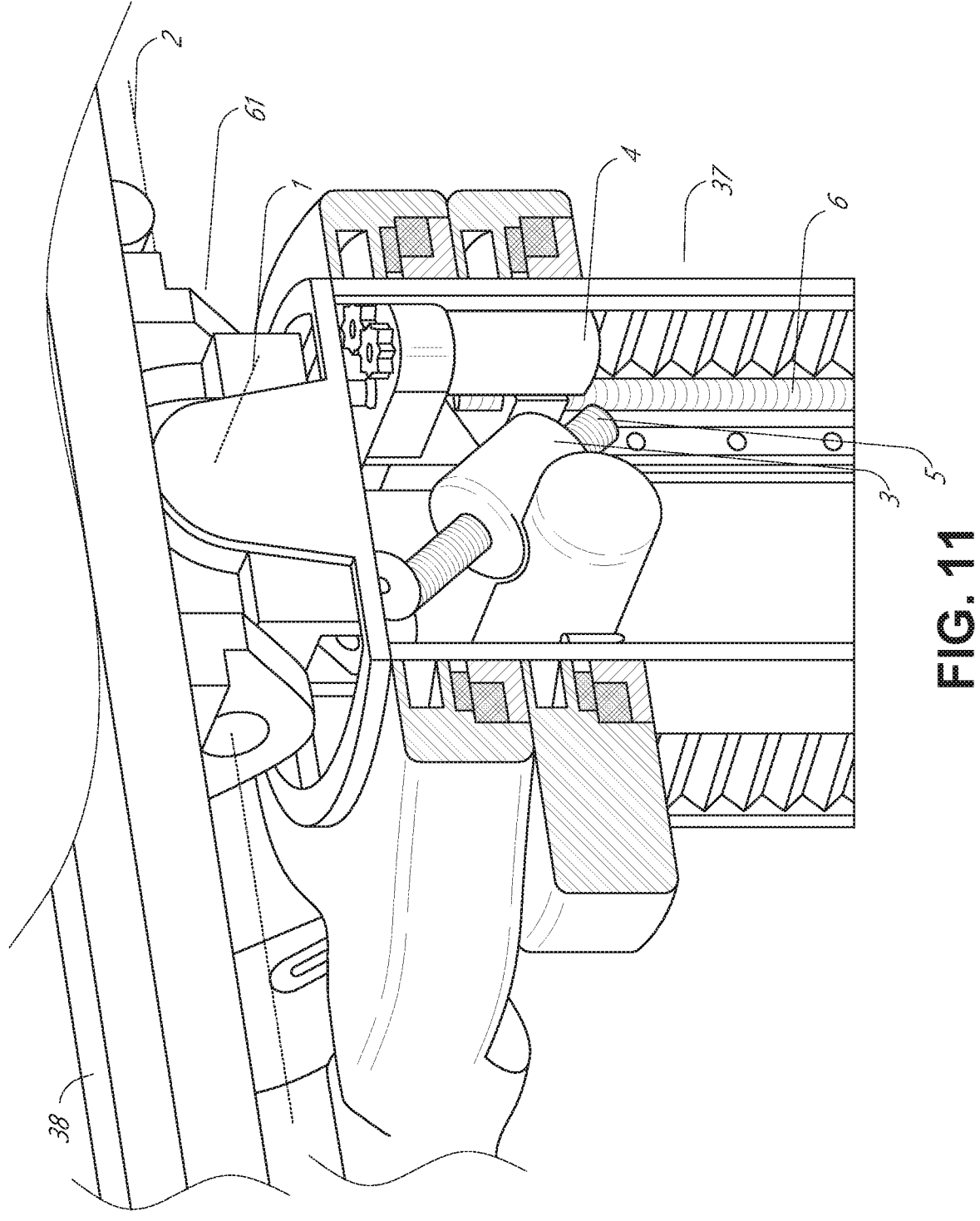
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
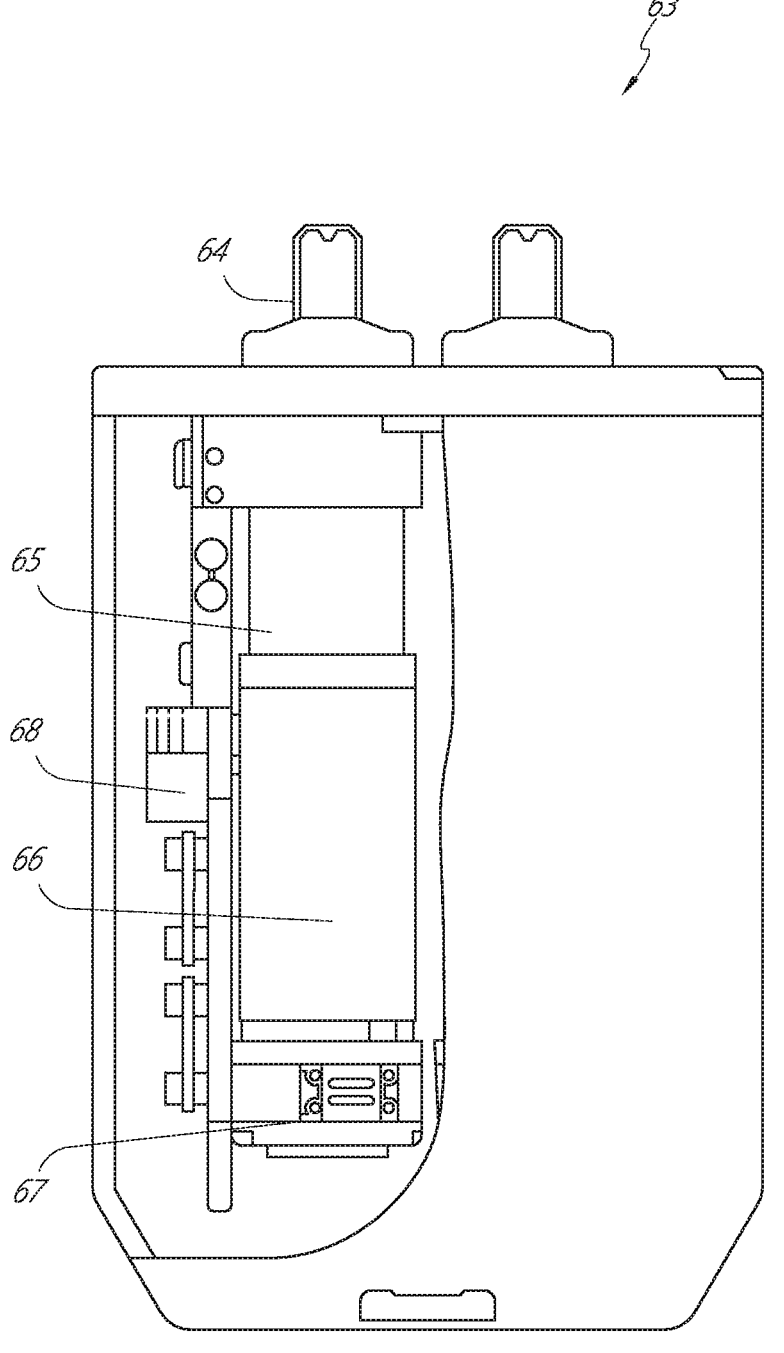
FIG. 12 illustrates an exemplary instrument driver.
Figure 12:

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
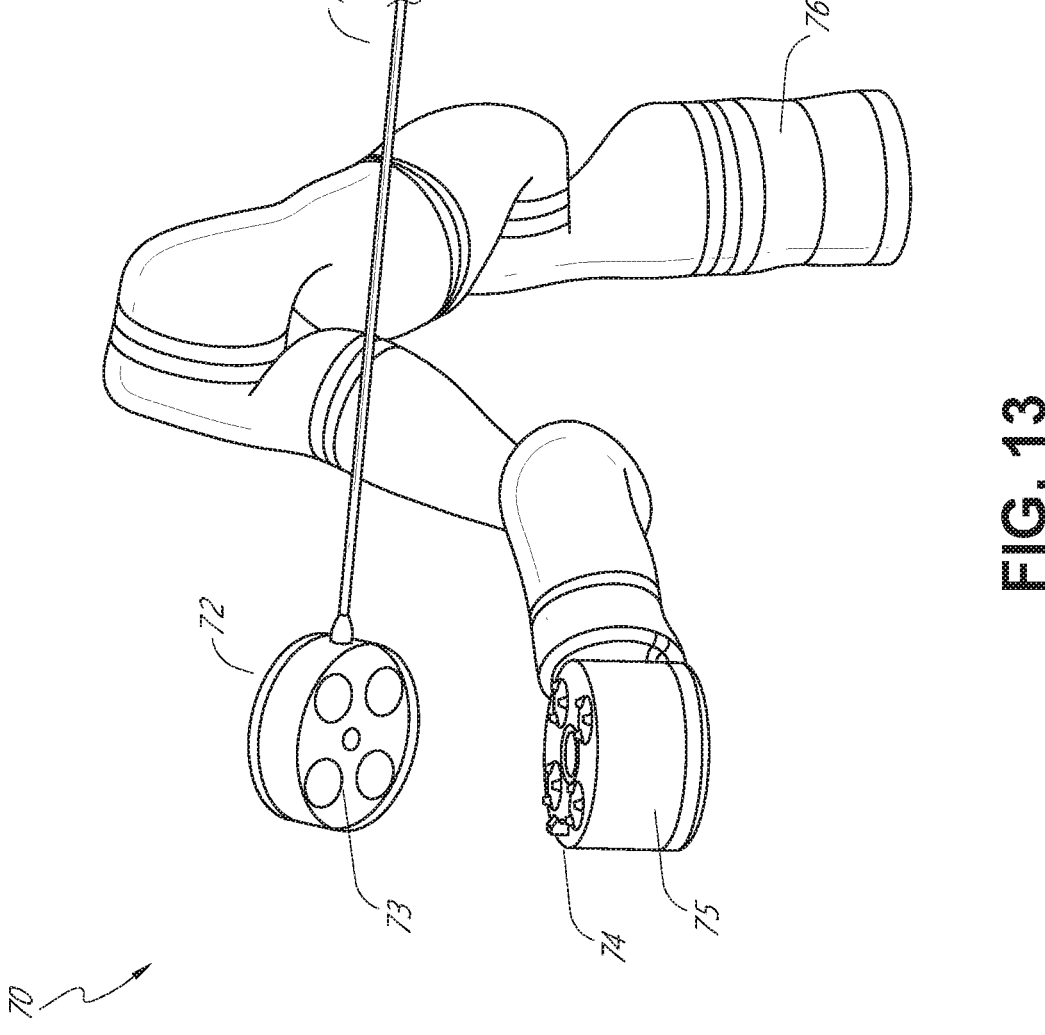
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
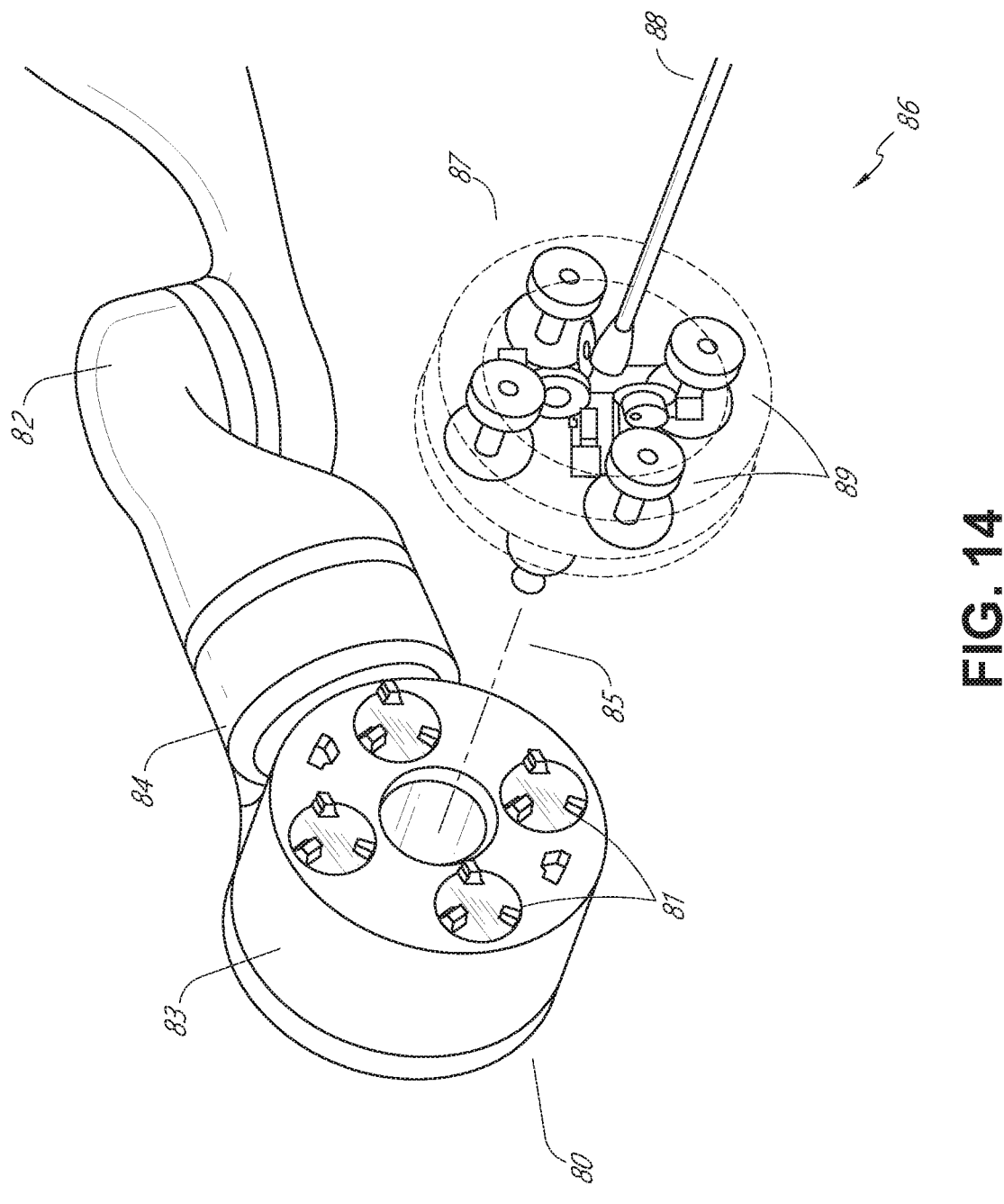
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons. E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
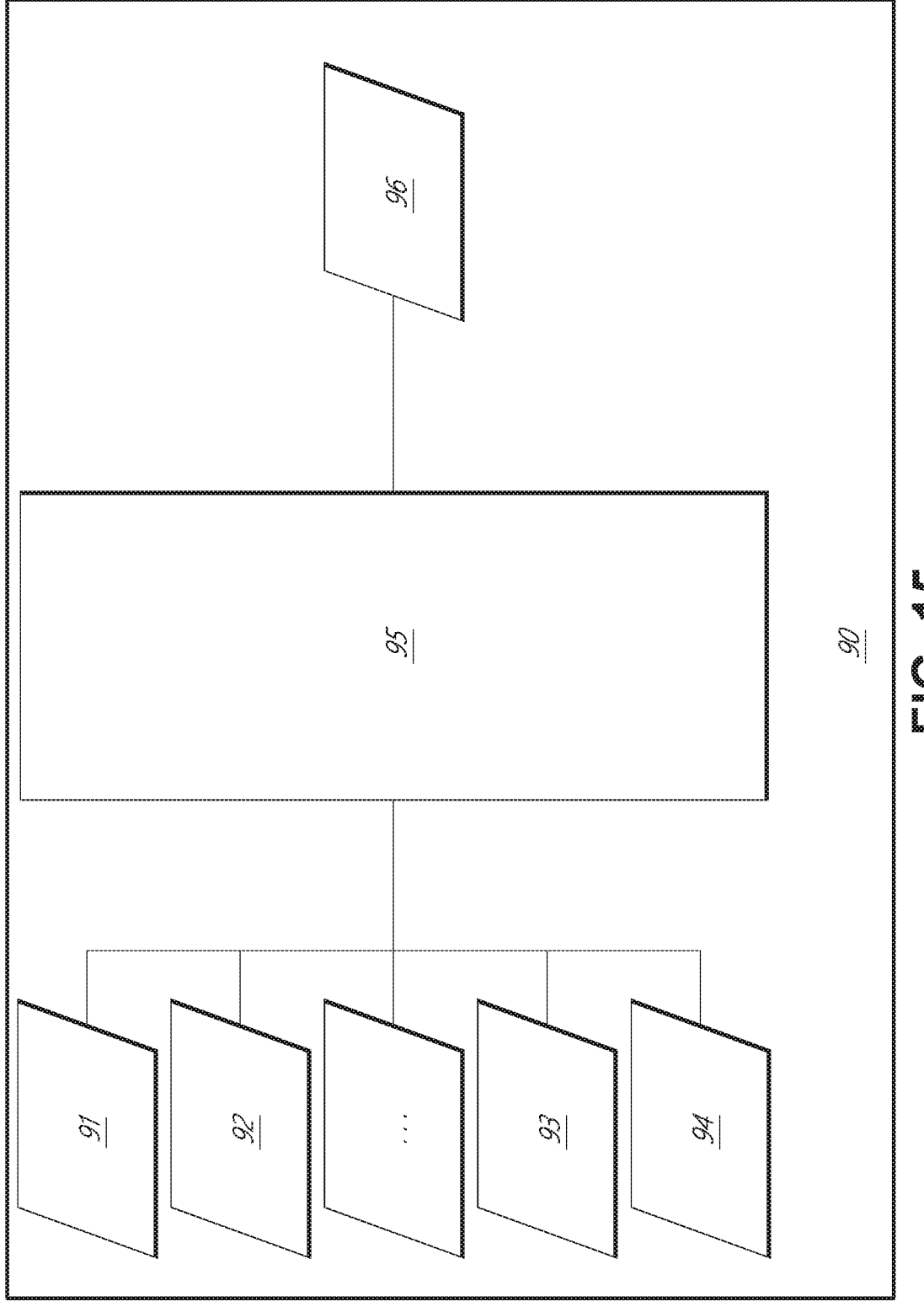
FIG. 15 depicts a block diagram illustrating a localization system that estimates a location of one or more elements of the robotic systems of FIGS. 1-10, such as the location of the instrument of FIGS. 13-14, in accordance to an example embodiment.

FIG. 15 is a block diagram illustrating a localization system 90 that estimates a location of one or more elements of the robotic system, such as the location of the instrument, in accordance with an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide location data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Estimating Instrument Location with Comparison of Location Input Data.

Robotically-enabled medical systems, such as those described above with reference to FIGS. 1-15, may be configured to provide an estimate of instrument position or location during a medical or surgical procedure, such as an endoscopic or laparoscopic procedure. During the procedure, a physician can guide or direct the instrument through an internal region (e.g., a lumen, a luminal network, a cavity, etc.) of a patient. To assist the physician, a location/position estimate for the instrument may be determined and displayed to the user, for example, with the localization system 90 (FIG. 15).

Figure 16:
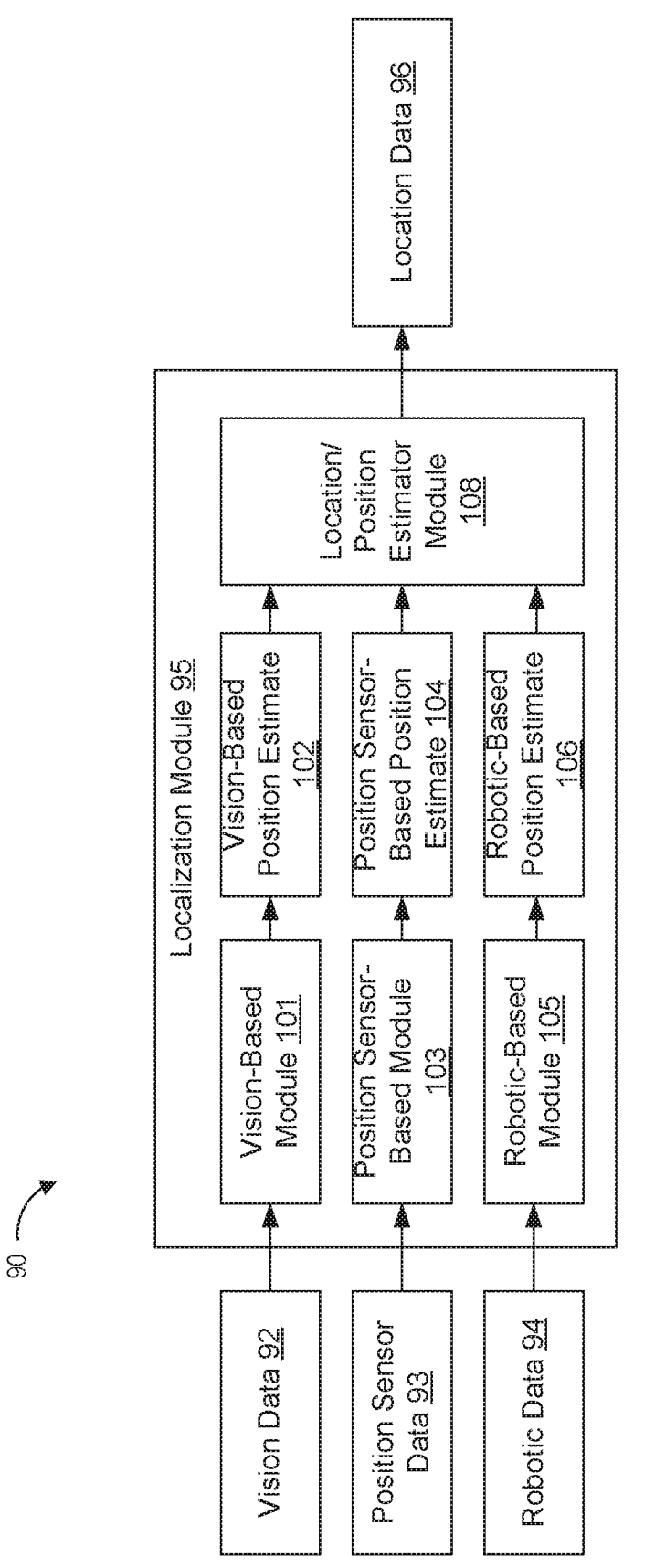
FIG. 16 depicts another block diagram illustrating the localization system of FIG. 15 in greater detail.

FIG. 16 depicts a block diagram illustrating an embodiment of localization system 90 in greater detail. In the illustrated example, the localization system 90 is configured to receive and process vision data 92, position sensor data 93 (e.g., EM data), and robotic data 94 (e.g., robotic command and kinematics data) and thereby provide location data 96 as an output. The location data 96 can include, for example, a position estimate for the instrument.

Although, the vision data 92, the position sensor data 93, and the robotic data 94 are illustrated as input data in FIG. 16, the localization system 90 may also receive and process additional types of input data as described above. As one example, the localization system 90 may also receive and process preoperative model data 91 as previously described.

As illustrated, the localization module 95 can include vision-based module 101, a position sensor-based module 103, and a robotic-based module 105. Each of the modules 101, 103, 105 can include software and/or hardware for receiving and processing the various input data. In some embodiments, one or more of the modules 101, 103, 105 may be combined with each other and/or with other modules (such as a location/position estimator module 108). Example modules are described in detail in U.S. application Ser. No. 15/268,238, filed Sep. 16, 2016, which issued as U.S. Pat. No. 9,727,963 on Aug. 8, 2017, and which is incorporated herein by reference.

The vision-based module 101 may be configured to receive and process the vision data 92. The vision data 92 may be received from an imaging device (e.g., fiberscope or camera). The imaging device may be positioned on the instrument. The vision data 92 can include one or more images or videos. The vision-based module 101 may be configured to determine a vision-based location/position estimate 102 from the vision data 92. For example, the vision-based module 101 can process images received from the instrument device positioned on the instrument to determine the position of the instrument relative to a preoperative model (e.g., the preoperative model data 91) as described above.

The position sensor-based module 103 may be configured to receive and process the position sensor data 93. The position sensor data 93 may be received from one or more position sensors. The position sensors may be positioned on the instrument. The position sensors may be, for example, EM sensors, shape-sensing fibers, accelerometers, gyroscopes, imaging devices, ultrasonic sensors, etc. The position sensor-based module 103 may be configured to determine a position sensor-based location/position estimate 104 from the position sensor data 93. For example, the position sensor-based module 103 can process data received from an EM sensor on the instrument to determine the position of the instrument relative to a coordinate frame of the preoperative model.

The robotic-based module 105 may be configured to receive and process the robotic data 94. The robotic data 94 can include insertion and/or articulation commands for controlling the shape and movement of the instrument. The robotic-based module 105 may be configured to determine a robotic-based location/position estimate 106 from the robotic data 94. For example, during the procedure, information for known or commanded insertion depth and/or articulation or roll angles for the instrument, as executed by one or more robotic arms or other instrument positioning devices, may be used to estimate the position of the instrument.

The vision-based position estimate 102, the position sensor-based position estimate 104, and the robotic-based position estimate 106 may be inputs into a location estimator module 108, as illustrated. Other inputs (not illustrated) may be provided to the location estimator module 108 as well. The location estimator module 108 may be implemented in hardware, software, or a combination thereof.

The location estimator module 108 may be configured to combine the vision-based position estimate 102, the position sensor-based position estimate 104, and/or the robotic-based position estimate 106 to output location data 96. The location estimator module 108 may determine the combination using a probabilistic approach that assigns a confidence weight (or weighting factor) to the vision-based position estimate 102, the position sensor-based position estimate 104, and/or the robotic-based position estimate 106. In some embodiments, the location estimator module 108, and/or another component or module of the localization system 90, may determine the weighting factor for each of the vision-based position estimate 102, the position sensor-based position estimate 104, and/or the robotic-based position estimate 106. The weighting factors may be used to increase or decrease the contribution of the vision-based position estimate 102, the position sensor-based position estimate 104, and/or the robotic-based position estimate 106 to the determination of the output location data 96.

For example, in some cases, one of the vision-based position estimate 102, the position sensor-based position estimate 104, and/or the robotic-based position estimate 106 may be determined to be less reliable than another of the vision-based position estimate 102, the position sensor-based position estimate 104, and/or the robotic-based position estimate 106. The weighting factor of the less reliable one(s) may be decreased and/or the weighting factor of the more reliable one(s) may be increased. As a result, the output location data 96 may provide a more reliable position estimate for the instrument because the more reliable inputs have been weighted more heavily.

As another example, the weighting factor for one or more of the vision-based position estimate 102, the position sensor-based position estimate 104, and/or the robotic-based position estimate 106 may be set to zero to eliminate contribution of one or more of those input estimates to the determination of the location data 96.

The location estimator module 108 (and/or other component(s) of the localization system 90, such as the vision-based module 101, the position sensor-based module 103, and/or the robotic-based module 105) may be configured to determine the weighting factors for each of the vision-based position estimate 102, the position sensor-based position estimate 104, and/or the robotic-based position estimate 106. In general, the weighting factors may be decreased when a particular input position estimate is determined to be unreliable and/or increased when a particular input position estimate is determined to be reliable.

An advantage of some of the robotically-enabled medical systems described herein is that they include localization systems 90 that process multiple types of input data (e.g., the vision data 92, the position sensor data 93, and/or the robotic data 94) to produce multiple position estimates (e.g., the vision-based position estimate 102, the position sensor-based position estimate 104, and/or the robotic-based position estimate 106) that are combined (e.g., according to weighting factors) to determine a position estimate (e.g., location data 96) for the instrument. This may be advantageous because, if a particular data input is determined to be less reliable (at a certain instance or in a certain situation), the contribution of that data input to the finally determined position estimate may be reduced or eliminated.

Additionally, the systems described herein may be advantageous because, since there are multiple data inputs and input position estimates, these may be compared to each other to determine the reliability and accuracy of the various data inputs and position estimates. As will be described below, comparison between multiple data inputs and input position estimates may be used to determine and/or set weighting factors. This can further improve the finally determined position estimate for the instrument, which can improved navigation and tracking of the instrument during a medical procedure.

The remainder of this disclosure describes how instrument position may be estimated and improved with comparison of input data or input position estimates. For ease of description, particular use cases of instrument buckling and instrument hysteresis are described by way of example. Other use cases are possible as well.

A. Example of Instrument Buckling.

This section describes instrument buckling and provides a first example where an instrument position estimate may be determined or improved with comparison of various input data or input position estimates.

Figures 17A, 17B:
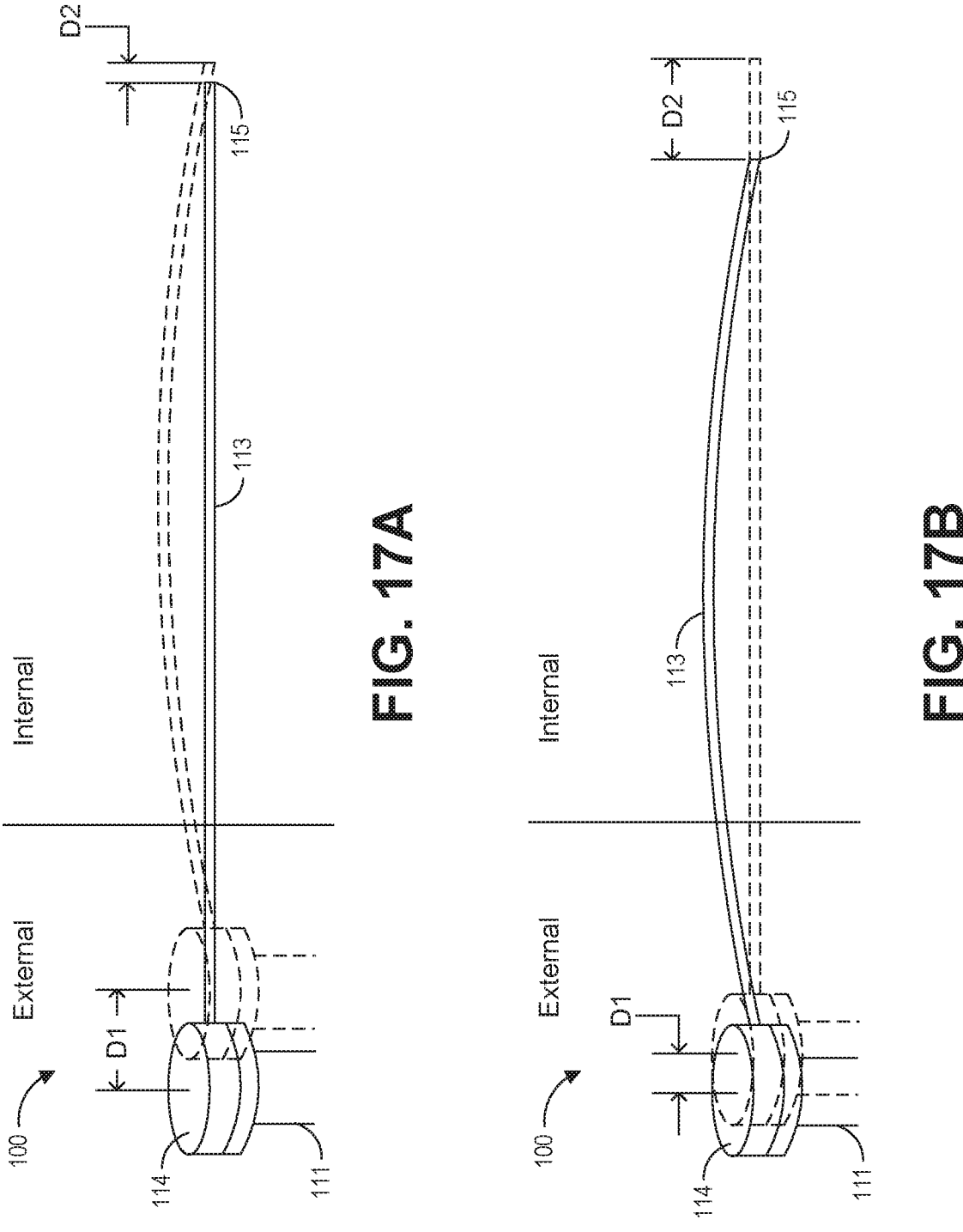
FIG. 17A illustrates an example of a medical instrument experiencing a buckling condition.
FIG. 17B illustrates an example of a medical instrument experiencing a hysteresis condition.

FIG. 17A illustrates an example of a medical instrument 100 experiencing a buckling condition. The instrument 100 may be, e.g., the endoscope 13 (FIG. 1), the ureteroscope 32 (FIG. 3), the instrument 34 (FIG. 4), the ureteroscope 56 (FIG. 8), the laparoscope 59 (FIG. 9), the instrument 70 (FIG. 13), or the instrument 86 (FIG. 14) described above, or any other medical instrument described herein, such as instrument 200 (described below with reference to FIG. 19). As illustrated in FIG. 17A, the instrument 100 includes an elongated shaft 113 extending between a proximal end 114 and a distal end 115. The proximal end 114 may be connected to an instrument driver of an instrument positioning device 111, such as a robotic arm. As described above, the instrument positioning device 111 can move to insert or retract the instrument 100 into a patient. The instrument positioning device 111 can also be configured to articulate (e.g., control the shape or pose) of the instrument 100. For ease of illustration, the anatomy of the patient is not illustrated beyond a general representation that a portion of the elongated shaft 113 (including the distal end 115) may be positioned internal to the patient and another portion of the elongated shaft 113 (including the proximal end 114) and the instrument positioning device 111 may be positioned external to the patient. It will be appreciated, however, that internal to the patient, the elongated shaft 113 may follow the general shape of the patient's anatomy into which the instrument 100 is inserted.

To illustrate a buckling condition, in FIG. 17A, a first state of the instrument 100 is illustrated in solid lines and a second state of the instrument 100 is illustrated in dashed lines. In the second state (dashed lines) the instrument 100 has buckled (i.e., experienced a buckling condition). As illustrated, moving from the first state to the second state, the instrument positioning device 111 has advanced a first distance D1. The proximal end 114 of the elongated shaft 113 of the instrument 100, which is attached to the instrument positioning device 111, has also advanced the distance D1. The distal end 115 of the elongated shaft 113, however, has advanced only a distance D2, which is less than the distance D1. As illustrated, the elongated shaft 113 has buckled, bowed, bent, deflected, or otherwise deformed in an unintended way, such that the instrument 100 has experienced a buckling condition as illustrated in dashed lines in FIG. 17A.

Buckling may occur, for example, when the instrument 100 is advanced into the patient. The instrument positioning device 111 may advance the instrument 100 into the patient the distance D1. Absent buckling, one would generally expect the distal tip 115 of the instrument 100 to also advance by the distance D1. In some cases, however, the distal tip 115 may become caught or blocked within the patient's anatomy, such that the distal tip 115 only advances the distance D2, which is less than the distance D1. In some instances, the distal tip 115 may not advance at all, such that the distance D2 is zero. When the distal tip 115 becomes caught or blocked, the instrument buckles, and the elongated shaft 113 deforms (e.g., buckles, bows, bends, or otherwise deforms) in an unintended way.

It should be appreciated that while FIG. 17A illustrates the elongated shaft 113 disposed in a generally straight manner in the first state (solid lines) and in a gently curved manner in the second or buckled state (dashed lines), in general, the elongated shaft 113 may follow the patient's anatomy when positioned within the body and buckling may be manifest by any number of deformations of the elongated shaft 113. Regardless of the shape formed by the elongated shaft 113, a buckling condition has occurred when a motion D2 at the distal end 115 is less than an anticipated motion of the distal end 115 based on, for example, a motion D1 at the proximal end 114.

A robotically-enabled medical system including the instrument 100 may be configured to provide a position estimate for, for example, the distal end 115 of the instrument 100. The system can include the localization system 90 described above (e.g., in FIGS. 15 and 16). As noted previously, the localization system 90 processes and combines multiple types of input data to determine the position estimate.

Movement of the instrument positioning device 111 can generate or be based on robotic data 94. For example, the robotic data 94 can indicate that the instrument 100 has moved forward by the distance D1. The robotic-based module 105 may process the robotic data 94 to provide a robotic-based position estimate 106, which indicates that the distal end 115 of the instrument 100 has advanced the distance D1 from its previous position. As shown, in FIG. 17A, however, the distal tip 115 has only advanced the distance D2 (not the distance D1) because the instrument 100 has buckled.

The localization system 90 may receive as an input the position sensor data 93 from a position sensor. In this example, the position sensor may be positioned at the distal end 115 of the elongated shaft 113. As the instrument 100 moves from the first state (solid lines) to the second state (dashed lines), the position sensor (positioned at the distal tip 115) can provide the position sensor data 93 to the localization system 90. The position sensor-based module 103 can process the position sensor data 93 to provide a position sensor-based position estimate 104 that indicates that the distal end 115 has advanced the distance D2.

The localization system 90 can compare the robotic-based position estimate 106 and the position sensor-based position estimate 104 to determine weighting factors for each. In this example, the localization system 90 can determine that the movement indicated by the robotic-based position estimate 106 exceeds the movement indicated by the position sensor-based position estimate 104 by the difference between D1 and D2. The localization system 90 may be configured to recognize from this difference that a buckling condition has occurred and may accordingly decrease the weighting factor for the robotic-based position estimate 106 and/or increase the weighting factor for the position sensor-based position estimate 104. The localization system 90 may then combine the robotic-based position estimate 106 the position sensor-based position estimate 104 according to the determined weighting factors to provide and output a position estimate for the instrument 100 as location data 96. Because the localization system 90 has determined that the instrument 100 has buckled (by comparing the robotic-based position estimate 106 and position sensor-based position estimate 104) and adjusted the weighting factors accordingly, the accuracy of the estimated position output as location data 96 may be improved.

Similar comparisons may be made between the vision-based position estimate 102 and the position sensor-based position estimate 104 and/or the robotic-based position estimate 106 to detect buckling and provide a position estimate with increased accuracy. These comparisons will be described in greater detail below following the discussion of the example of instrument hysteresis.

B. Example of Instrument Hysteresis.

Instrument hysteresis provides another example that illustrates that an instrument position estimate may be determined or improved with comparison of various input data or input position estimates. It is to be appreciated that the term "hysteresis," as used herein, may refer to a specific class of hysteresis condition that a medical instrument can experience. This specific class of hysteresis may relate to the condition where a medical instrument returns or transitions towards a natural state from a deformed shape. A very specific example is where a medical device returns from a buckled state to a unbuckled state (or a less buckled state). An example of this type of hysteresis condition is now explained.

FIG. 17B illustrates an example of the medical instrument 100 experiencing a type of hysteresis condition. As before, the instrument 100 may be, e.g., the endoscope 13 (FIG. 1), the ureteroscope 32 (FIG. 3), the instrument 34 (FIG. 4), the ureteroscope 56 (FIG. 8), the laparoscope 59 (FIG. 9), the instrument 70 (FIG. 13), or the instrument 86 (FIG. 14) described above, or any other medical instrument described herein, such as the instrument 200 (FIG. 19) described below.

In FIG. 17B, a first state of the instrument 100 is illustrated in solid lines and a second state of the instrument 100 is illustrated in dashed lines. In the second state (dashed lines), the instrument 100 has experienced hysteresis. As illustrated, in the first state (solid lines) the elongated shaft 113 of the instrument 100 is in a buckled, bowed, bent, or deflected position. Moving from the first state to the second state, the instrument positioning device 111 may advance a first distance D1. The proximal end 114 of the elongated shaft 113 of the instrument 100, which is attached to the instrument positioning device 111, also advances the distance D1. In some examples of hysteresis, the instrument positioning device 111 and the proximal end 114 may not advance at all (i.e., the distance D1 may be zero).

When the instrument 100 experiences hysteresis, however, the distal end 115 of the elongated shaft 113 advances a distance D2, which is greater than the distance D1. This may be caused by the buckled, bowed, bent, or deflected elongated shaft 113 of the instrument relaxing to a more extended position. Hysteresis may also occur when an instrument 113 which is blocked or caught on the patient anatomy suddenly becomes free. In both of these cases, the distal end 115 advances a distance D2, which is greater than the distance D1 advanced by the proximal end 114 and instrument positioning device 111.

Again, it should be appreciated that while FIG. 17B illustrates the elongated shaft 113 disposed in a generally curved manner in the first state (solid lines) and in a gently straight manner in the second state (dashed lines), in general, the elongated shaft 113 may follow the patient's anatomy when positioned within the body and hysteresis may be manifest with the elongated shaft 113 in any number of positions. Regardless of the shape formed by the elongated shaft 113, a hysteresis condition has occurred when a motion D2 at the distal end 115 is greater than an anticipated motion at the distal end 115 based on, for example, a motion D1 at the proximal end 114.

In terms of the localization system 90, during a hysteresis condition, movement of the instrument positioning device 111 can generate robotic data 94. The robotic data 94 can indicate that the instrument 100 has moved forward by the distance D1. The robotic-based module 105 may process robotic data 94 to provide a robotic-based position estimate 106, which indicates that the distal end 115 of the instrument 100 has advanced the distance D1 from its previous position. As shown in FIG. 17B, however, the distal tip 115 has advanced the distance D2 because the instrument 100 has experienced hysteresis.

As the instrument 100 moves from the first state (solid lines) to the second state (dashed lines), a position sensor (positioned at the distal tip 115) can provide position sensor data 93 to the localization system 90. The position sensor-based module 103 can process the position sensor data 93 to provide a position sensor-based position estimate 104 that indicates that the distal end 115 has advanced the distance D2.

The localization system 90 can compare the robotic-based position estimate 106 and the position sensor-based position estimate 104 to determine weighting factors for each. In this example, the localization system 90 can determine that the movement indicated by the position sensor-based position estimate 104 exceeds the movement indicated by the robotic-based position estimate 106 by the difference between D1 and D2. The localization system 90 may be configured to recognize from this difference that a hysteresis condition has occurred and may accordingly, decrease the weighting factor for the robotic-based position estimate 106 and increase the weighting factor for the position sensor-based position estimate 104. The localization system 90 may then combine the robotic-based position estimate 106 and the position sensor-based position estimate 104 according to the determined weighting factors to determine and output a position estimate for the instrument as location data 96. Because the localization system 90 has determined that the instrument 100 has experienced a hysteresis condition (by comparing the robotic-based position estimate 106 and the position sensor-based position estimate 104) and adjusted the weighting factors accordingly, the accuracy of the estimated position output as location data 96 may be improved.

Similar comparisons may be made between the vision-based position estimate 102 and the position sensor-based position estimate 104 and/or the robotic-based position estimate 106 to detect hysteresis and provide a position estimate with increased accuracy. These comparisons will be described in greater detail below.

C. Example Methods for Determining Instrument Position with Comparison of Input Data.

Figure 18A:
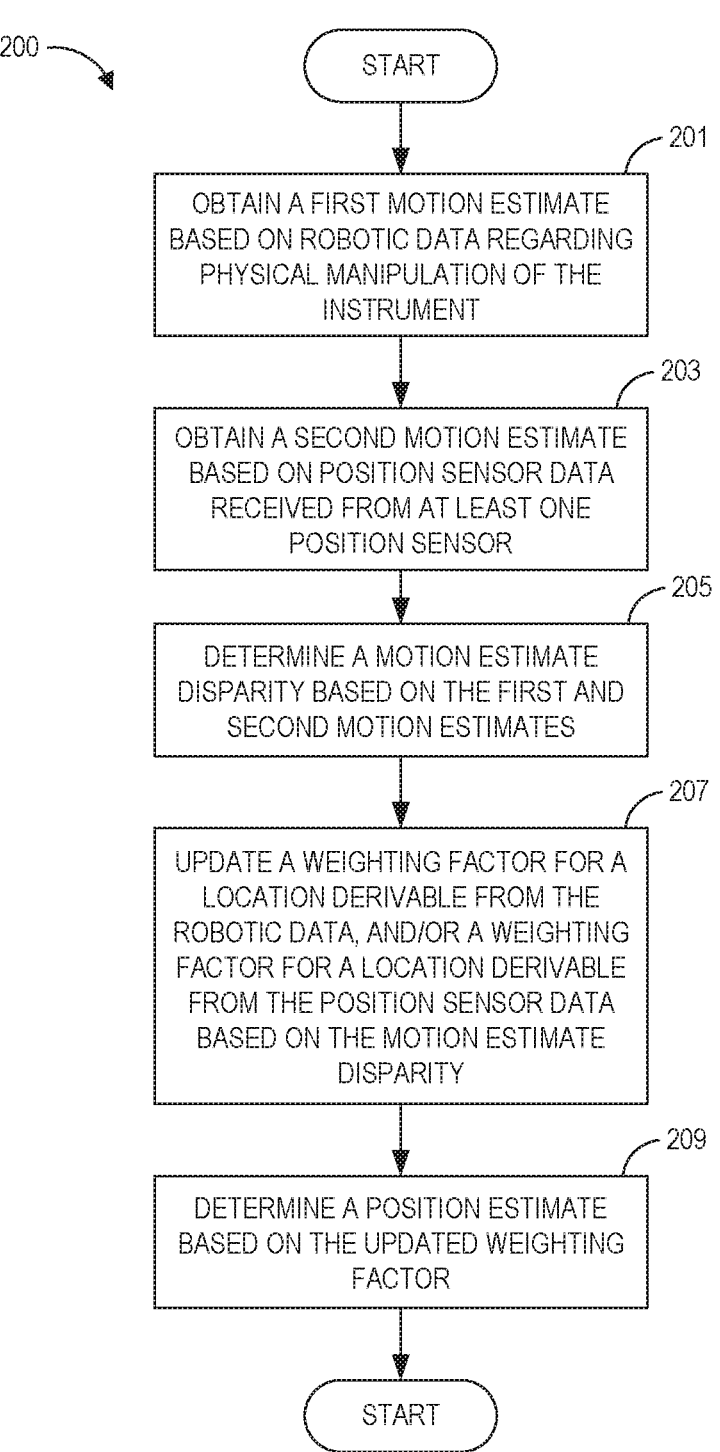
FIG. 18A is a flowchart illustrating an example method for determining a location/position estimate for a medical instrument based on a comparison of robotic data and position sensor data.

FIG. 18A is a flowchart illustrating an example method 200 for determining or improving the accuracy of a position estimate for the medical instrument 100 based on a comparison of the robotic data 94 and the position sensor data 93. The method 200 may be implemented in certain robotic systems, such as the robotic systems illustrated in FIGS. 1-15 and others. The method 200 may be implemented in or by localization system 90 of FIGS. 15 and 16. In some embodiments, one or more computer devices may be configured to execute the method 200. The computer devices may be embodied by a processor (or processors) and computer-readable memory in one or more components discussed above. The computer-readable memory may store instructions that may be executed by the processor(s) to perform the method 200. The instructions may include one or more software modules. By way of example and not limitation, the computer devices may be in the tower 30 shown in FIG. 1, the cart shown in FIGS. 1-4, the beds shown in FIGS. 5-10, etc.

The method 200 shown in FIG. 18A begins at block 201. At block 201, a first motion estimate for an instrument is obtained based on robotic data (e.g., the robotic data 94) regarding physical manipulation of the instrument. As discussed above, the robotic data 94 can include data related to physical movement of the instrument 100 or part of the instrument (e.g., the distal end 115). An example of robotic data 94 can include command data instructing the distal end 115 to reach a specific anatomical site and/or change its orientation (e.g., with a specific pitch, roll, yaw, insertion, and/or retraction). The robotic data 94 can include data representing mechanical movement of the elongated shaft 113 of the instrument 100, for example motion of one or more pull wires or tendons to drive the actual movement or control the pose of the medical instrument 100. The robotic data 94 can include data relating to the movement of one or more of the instrument positioning devices 111, such as the robotic arms described previously. Positions or movement (changes in position) may be determined from the robotic data 94.

The motion estimate can include an estimate of the movement of the instrument 100. The motion estimate may be determined over an interval. In some implementations, the interval is a time interval. For example, at block 201, the method 200 can involve determining an estimate, based on the robotic data 94, for the change in position during a time interval such as about 0.1 seconds, 0.2 seconds, 0.25 seconds, 0.5 seconds, 0.75 seconds, 1 second, 1.5 seconds, 2 seconds, or 5 seconds. Other time intervals, both shorter and longer than these listed examples are also possible.

In some implementations, the interval is a distance interval. For example, at block 201, the method 200 can involve determining an estimate, based on the robotic data 94, for the change in position during a distance interval such as about 0.1 mm, 0.2 mm, 0.25 mm, 0.5 mm, 0.75 mm, 1 mm, 1.5 mm, 2 mm, 5 mm, 10 mm, 15 mm, 20 mm, 25 mm, 30 mm, 35 mm, 40 mm, 45 mm, or 50 mm. Other distance intervals, both shorter and longer than these listed examples are also possible. The distance interval may represent a distance moved by the instrument position device 111, the proximal end 114 of the elongated shaft 113, and/or the distal end 115 of the elongated shaft 113; a commanded insertion distance; a commanded travel distance of the instrument 100; a measured insertion distance; a measured travel distance of the instrument 100; an estimated travel distance of the instrument 100 as determined by the vision-based module 101, the position-sensor-based module 103, the robotic-based module 105, and/or the location estimator module 108, etc.

In some implementations, the interval is a rolling window or frame. The interval may be a rolling window or frame of time or distance, providing a motion estimate for the instrument 100 over a time or distance window immediately preceding the current time point. For example, at each time point, block 201 can involve determining a new motion estimate representing a change in position over a time interval immediately preceding the each time point.

In some implementations, block 201 involves obtaining the motion estimate from the robotic data 91 in conjunction with one or more other data inputs. For example, the motion estimate may be determined at block 201 using one or both the robotic data 91 and the preoperative model data 94, for example.

At block 203, a second motion estimate is obtained based on position sensor data (e.g., the position sensor data 93) received from at least one position sensor. As discussed above, the position sensor data 93 may be received from one or more position sensors. In some implementations, the position sensor is positioned on the instrument 100, for example, on the distal end 114 of the instrument 100. A position of the position sensor may be derived from the position sensor data 93 relative to a coordinate frame. The coordinate frame for the position sensor may be registered to a coordinate frame of the preoperative model, such that the position may be determined relative to the preoperative model.

The position sensor may be any type of sensor for determining position. For example, the position sensor may be an EM sensor as described above. The EM sensor can provide position sensor data 93 from which the position of the EM sensor may be derived relative to an EM field produced by an EM field generator. In another example, the position sensor may be an EM field generator positioned on the instrument, and the position of the EM field generator may be determined relative to EM sensors positioned outside of the patient's body.

In other examples, the position sensor can be a shape-sensing fiber, an accelerometer, a gyroscope, and/or an ultrasonic sensor. In another example, the position sensor may be an imaging device. The imaging device may be positioned on the instrument. The output of the imaging device (e.g., images or video) may be analyzed to determine positional information.

A motion estimate may be obtained from the position sensor data 93 by analyzing the position sensor data 93 during an interval. In some implementations, the interval may be a time or distance interval as described above. The interval may be a rolling interval or frame.

In some implementations, the interval used for obtaining the motion estimate from the position sensor data 93 may be the same interval as the interval used for obtaining the motion estimate from the robotic data 94. For example, the intervals used at block 203 may match the interval used at block 201.

In some embodiments the order of block 201 and block 203 may vary. In some embodiments, block 201 and block 203 may occur at substantially the same time.

At block 205, the method 200 involves determining a motion estimate disparity based on a comparison of the first motion estimate and the second motion estimate. The motion estimate disparity may be representative or indicative of a difference between the motion estimate obtained from the robotic data 94 at block 201 and the motion estimate obtained from the position sensor data 93 at block 203. In some implementations, determining the motion estimate disparity involves taking a difference between the motion estimate obtained from the robotic data 94 at block 201 and the motion estimate obtained from the position sensor data 93 at block 203. In some embodiments, determining the motion estimate disparity involves taking a difference between a final position obtained from the robotic data 94 (e.g., during the interval) and a final position obtained from the position sensor data 93 (during the interval).

At block 207, the method 200 involves, based on the motion estimate disparity, updating: (a) a weighting factor for a location derivable from the robotic data (e.g., the robotic data 94), and/or (b) a weighting factor for a location derivable from the position sensor data (e.g., the position sensor data 93). As discussed above, the localization system 90 can use the weighting factors when combining the positions estimated from the different types of input data.

For example, block 207 can involve decreasing the weighting factor for a location derivable from the robotic data 94, and/or increasing the weighting factor for a location derivable from the position sensor data 93, when the motion estimate disparity indicates that the motion estimate based on the robotic data 94 (block 201) exceeds the motion estimate based on the position sensor data 93 (block 203). The motion estimate based on the robotic data 94 exceeding the motion estimate based on the position sensor data 93 may indicate that the instrument 100 has experienced a buckling condition. For example, as shown in FIG. 17A, buckling can occur when the instrument positioning device 111 and proximal end 114 of the instrument 100 move a greater distance than the distal end 115 of the instrument 100. In such a case, the motion estimate disparity indicates buckling because the motion estimate based on the robotic data 94 exceeds the motion estimate based on the position sensor data 93. Block 207 can involve decreasing the weighting factor for a location derivable from the robotic data 94, and/or increasing the weighting factor for a location derivable from the position sensor data 93. As a result, the localization system 90 outputs location data 96 that is derived more from the position sensor data 93 and less from the robotic data 94. This may result in a more accurate estimate of position for the instrument 100.

As another example, block 207 can involve decreasing the weighting factor for a location derivable from the robotic data 94, and/or increasing the weighting factor for a location derivable from the position sensor data 93, when the motion estimate disparity indicates that the motion estimate based on the position sensor data 93 (block 203) exceeds the motion estimate based on the robotic data 94 (block 201). The motion estimate based on the position sensor data 93 exceeding the motion estimate based on the robotic data 94 may indicate that the instrument 100 has experienced a hysteresis condition. For example, as shown in FIG. 17B, hysteresis can occur when the distal end 115 of the instrument 100 moves a greater distance than the instrument positioning device 111 and proximal end 114 of the instrument 100. In such a case, the motion estimate disparity indicates hysteresis because the motion estimate based on the position sensor data 93 exceeds the motion estimate based on the robotic data 94. Block 207 can involve decreasing the weighting factor for a location derivable from the robotic data 94, and/or increasing the weighting factor for a location derivable from the position sensor data 93. As a result, the localization system 90 outputs location data 96 that is derived more from the position sensor data 93 and less from the robotic data 94. This may result in a more accurate estimate of position for the instrument 100.

In some implementations, the weighting factor for a location derivable from the robotic data 94 is decreased, and/or the weighting factor for a location derivable from the position sensor data 93 is increased in a manner related to the magnitude of the motion estimate disparity. For example, the greater the motion estimate disparity, the greater the increase and/or decrease of the respective weighting factor (s). In some embodiments, the weighting factor(s) are increased and/or decreased in proportion to the magnitude of the motion estimate disparity.

In some embodiments, the weighting factor(s) are updated only when the motion estimate disparity exceeds a threshold value. For example, a motion estimate disparity greater than a threshold value can indicate a buckling or hysteresis condition. The threshold value may be a distance, such as about 5 mm, 10 mm, 15 mm, 20 mm, 25 mm, 30 mm, 35 mm, 40 mm, 45 mm, 50 mm, 55 mm, or 60 mm. Other distances for the threshold, both shorter and longer than these listed examples are also possible.

In some embodiments, decreasing a weighting factor can include setting the weighting factor to zero, such that the related input data is not used at all in determining the location data 96 output from the localization system 90. For example, in some implementations, block 207 can involve updating the weighting factor for a location derivable from the robotic data 94 to zero. That is, in some implementations, when the motion estimate disparity indicates buckling or hysteresis, the weighting factor for a location derivable from the robotic data 94 is set to zero, such that the robotic data 94 is not used to determine the final position estimate for the instrument 100.

At block 209, a location/position estimate based on the updated weighting factor is determined. As described previously, the position estimate may be output from the localization system 90 as location data 96. The localization system 90 determines the position estimate based on one or more of the input data 91-94 and weights the contribution of each input data according to the associated weighting factor(s). Accordingly, the method 200 can provide improved estimated positions for the instrument by reducing the contribution of the robotic data 94 and/or increasing the contribution of the position sensor data 93 in cases where, for example, the instrument 100 has experienced a buckling or hysteresis condition.

In some embodiments, the method 200 can also include providing an indication or alert that the instrument 100 has experienced a hysteresis or buckling condition. For example, when the motion estimate disparity indicates hysteresis or buckling, an indication (e.g., a visual or audio alert) can be provided to the physician. In another example, upon detection of a hysteresis or buckling condition, the method 200 can move (or modify movement) of the instrument 100. For example, the system may relax or reduce moment of the instrument. In some instances, action taken is at least partially dependent on the degree of the motion estimate disparity. For example, for motion estimate disparities below a certain threshold, the system may provide an alert, while for motion estimate disparities above a certain threshold, the system may relax or reduce moment of the instrument.

Some additional details for calculating estimated distances are now discussed before proceeding with the remaining disclosure. As discussed above, a rolling distance window may be used to compare estimated changes in movement determined from sensor locations (e.g., position sensor data 93) and robot commands (e.g. robotic data 94). The rolling window can be a data structure that stores the disparity as pairs of movement determined from sensor locations SL and movement determined from robot data RD. Thus, for a given point t, the disparity can be calculated by finding the difference between $SL_t$ and $RD_t$. In another embodiment, rather than storing data that can be used to derive the disparity, the rolling window simply includes, for each point t, the disparity. The data structure used to store the values in the rolling window may include an array, multi-dimensional array, look-up table, or any other suitable data structure.

Much of the discussion herein focuses on a comparison of the disparity between movements determined from robot data and sensor locations. However, this approach alone may result in false positives. Such may be the case where the instrument is commanded to articulate (e.g., angular movement in a flexible device or via a wrist structure), which would result in no movement data in the robot data but some movement in the location sensor. To avoid such false-positives, the system may re-initialize the window (or windows) used to track historical disparities when robot data indicates that an articulation command is executed. The system may re-initialize the window by zeroing out the data structure used to store the window of value. As initializing the window results in a loss of data, which may in turn result in failing to detect buckling, the system may use an articulation threshold to re-initialize the window only when an articulation command exceeds some angular amount. This would limit re-initialization for larger articulations which may have a larger impact on causing false positives.

Figure 18B:
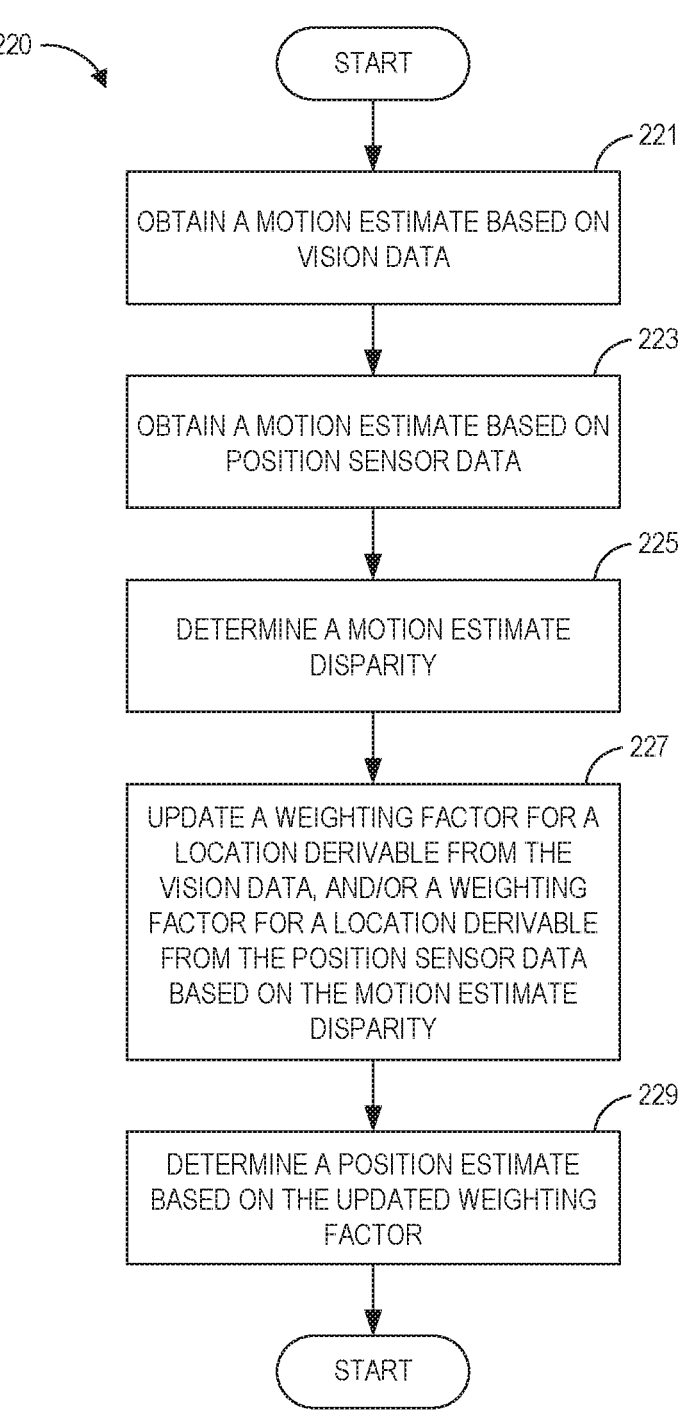
FIG. 18B is a flowchart illustrating an example method for determining a location/position estimate for a medical instrument based on a comparison of vision data and position sensor data.

FIG. 18B is a flowchart illustrating an example method 220 for determining a position estimate for the medical instrument 100 based on a comparison of vision data 92 and position sensor data 93. The method 220 may be implemented in certain robotic systems, such as the robotic systems illustrated in FIGS. 1-15 and others. The method 220 may be implemented in or by localization system 90 of FIGS. 15 and 16. In some embodiments, one or more computer devices may be configured to execute the method 200. The computer devices may be embodied by a processor (or processors) and computer-readable memory in one or more components discussed above. The computer-readable memory may store instructions that may be executed by the processor(s) to perform the method 220. The instructions may include one or more software modules. By way of example and not limitation, the computer devices may be in the tower 30 shown in FIG. 1, the cart shown in FIGS. 1-4, the beds shown in FIGS. 5-10, etc.

The method 220 begins at block 221. At block 221, a motion estimate is obtained based on vision data 92. As described above, vision data 92 may be received from an imaging device. The imaging device may be positioned on the instrument 100. The vision data 92 can include images or video. Vision data 92 may be used to determine a position estimate in a variety of ways. For example, an object-based analysis of the vision data 92 can detect and analyze objects present in the field of view of the vision data 92, such as branch openings or particles, to determine position. In some implantations, the vision data 92 is analyzed in conjunction with one or more other data inputs. For example, vision data 92 may be analyzed in conjunction with one or both of the robotic data 94 and preoperative model data 91 to determine a vision-based position estimate At block 221, a vision-based motion estimate may be determined based on the position estimates derived from the vision data 92. For example, a change in position over an interval may be determined may be determined. In some implementations, the interval may be a time or distance interval as described above. The interval may be a rolling interval or frame.

At block 223, a motion estimate is obtained based on position sensor data 93. Block 223 may be substantially similar to the block 203 previously described. In some embodiments, the motion estimate obtained based on the position sensor data 93 is determined over the same interval as the motion estimate based on the vision data 92. For example, the intervals used at block 203 may match the interval used at block 201.

In some embodiments the order of block 221 and block 223 may vary. In some embodiments, block 221 and block 223 may occur at substantially the same time.

At block 225, the method 220 involves determining a motion estimate disparity. The motion estimate disparity may be representative or indicative of a difference between the motion estimate obtained from the vision data 92 at block 221 and the motion estimate obtained from the position sensor data 93 at block 223. The motion estimate disparity may be determined as described above.

At block 227, the method 227 involves updating a weighting factor for a location derivable from the vision data 92, and/or a weighting factor derivable from the position sensor data 93. For example, block 227 can involve decreasing the weighting factor for a location derivable from the vision data 92, and/or increasing the weighting factor for a location derivable from the position sensor data 93, when the motion estimate disparity indicates that the motion estimate based on the vision data 92 (block 221) exceeds the motion estimate based on the position sensor data 93 (block 223). The motion estimate based on the vision data 92 exceeding the motion estimate based on the position sensor data 93 may indicate that the instrument 100 has experienced a buckling condition (FIG. 17A). In such a case, the motion estimate disparity indicates buckling because the motion estimate based on the vision data 92 exceeds the motion estimate based on the position sensor data 93. Accordingly, block 207 can involve decreasing the weighting factor for a location derivable from the vision data 92, and/or increasing the weighting factor for a location derivable from the position sensor data 93. As a result, the localization system 90 outputs location data 96 that is derived more from the position sensor data 93 and less from the vision data 92. This may result in a more accurate estimate of position for the instrument 100.

As another example, block 227 can involve decreasing the weighting factor for a location derivable from the vision data 92, and/or increasing the weighting factor for a location derivable from the position sensor data 93 when the motion estimate disparity indicates that the motion estimate based on the position sensor data 93 (block 223) exceeds the motion estimate based on the vision data 92 (block 221). The motion estimate based on the position sensor data 93 exceeding the motion estimate based on the robotic data 94 may indicate that the instrument 100 has experienced a hysteresis condition (FIG. 17B). In such a case, the motion estimate disparity indicates hysteresis because the motion estimate based on the position sensor data 93 exceeds the motion estimate based on the vision data 92. Accordingly, block 227 can involve decreasing the weighting factor for a location derivable from the vision data 92, and/or increasing the weighting factor for a location derivable from the position sensor data 93. As a result, the localization system 90 outputs location data 96 that is derived more from the position sensor data 93 and less from the vision data 92. This may result in a more accurate estimate of position for the instrument 100.

The weighting factor for a location derivable from the vision data 92 may be decreased, and/or the weighting factor for a location derivable from the position sensor data 93 may be increased in a manner similar to that discussed above with regard to block 207 of method 200.

At block 229, a location/position estimate based on the updated weighting factor is determined. As described previously, the position estimate may be output from the localization system 90 as location data 96. The localization system 90 determines the position estimate based on one or more of the input data 91-94 and weights the contribution of each input data according to the associated weighting factor. Accordingly, the method 220 can provide improved estimated positions for the instrument by reducing the contribution of the vision data 92 and/or increasing the contribution of the position sensor data 93 in cases where, for example, the instrument 100 has experienced a buckling or hysteresis condition.

D. Example Systems for Determining Instrument Position with Comparison of Input Data.

Figure 19:
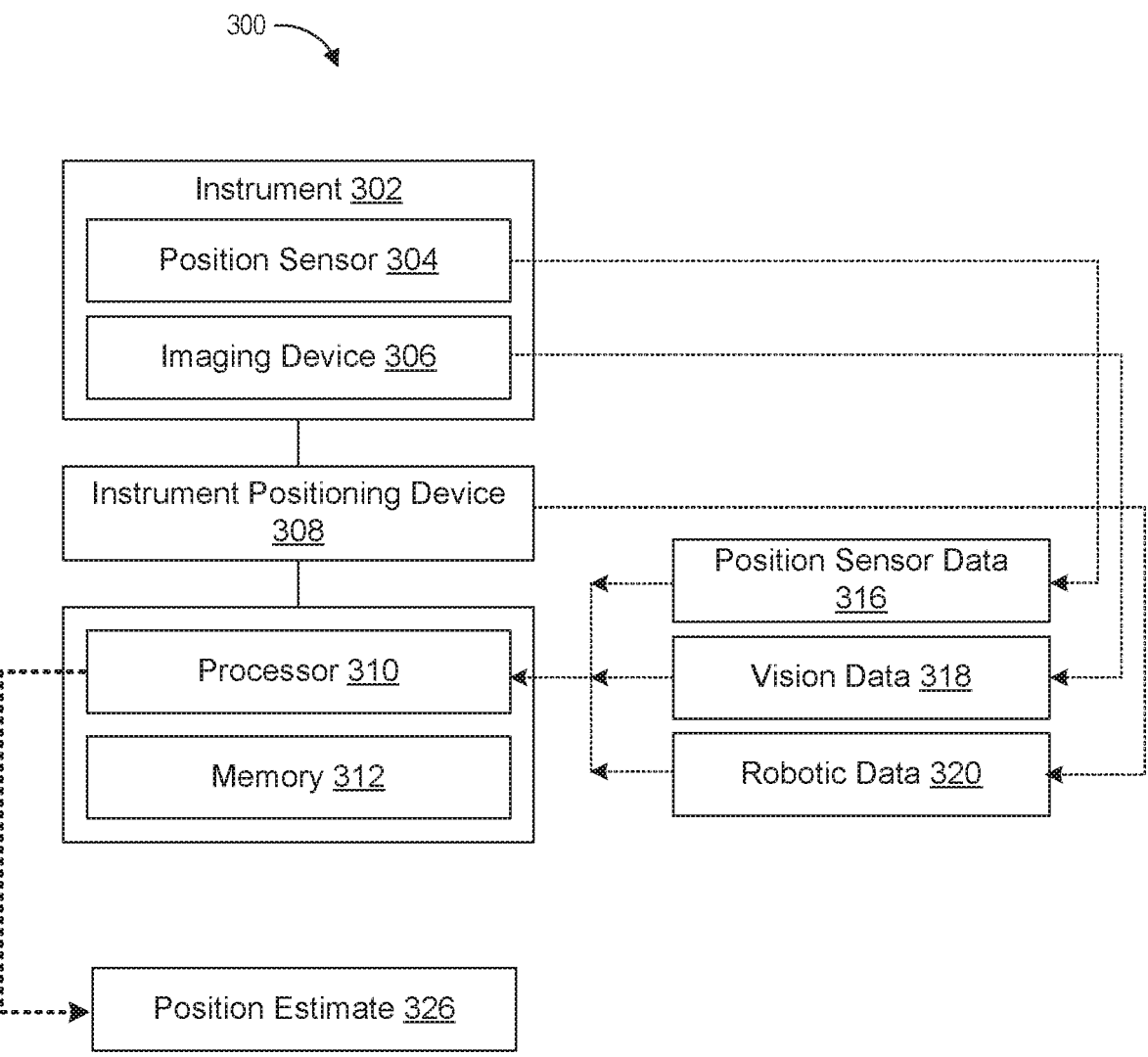
FIG. 19 is a block diagram illustrating an embodiment or a robotically-enabled medical system configured to provide an estimate of instrument location with comparison of location input data.

FIG. 19 is a block diagram illustrating an embodiment or a robotically-enabled medical system 300 configured to provide an estimate of instrument location with comparison of location input data using the methods described herein. The system 300 includes a processor 310 and memory 312. The memory 312 can store instructions that configure or instruct the processor 310 to execute, for example, the methods 200 and/or 220 described above.

The system 300 also includes an instrument 302. The instrument 302 may be, e.g., the endoscope 13 (FIG. 1), the ureteroscope 32 (FIG. 3), the instrument 34 (FIG. 4), the ureteroscope 56 (FIG. 8), the laparoscope 59 (FIG. 9), the instrument 70 (FIG. 13), the instrument 86 (FIG. 14), or the instrument 100 described above, or any other medical instrument described herein, or variation(s) thereof. The instrument 302 may include a position sensor 304 and an imaging device 306. The instrument 302 may be attached to an instrument positioning device 308 and configured to manipulate and move the instrument 302. The instrument positioning device 308 may be a robotic arm or component(s) thereof. The instrument positioning device 308 may be controlled by a processor 310 in some embodiments.

The position sensor data 316 may be received from and/or generated by the position sensor 304. The position sensor 304 may be positioned on the instrument 302. The position sensor may be a shape-sensing fiber, an accelerometer, a gyroscope, an electromagnetic sensor, an imaging device, or an ultrasonic sensor.

The vision data 318 may be received from and/or generated by the imaging device 306. The imaging device 306 may be positioned on the instrument 304. The imaging device 306 may be any photosensitive substrate or structure configured to convert energy representing received light into electric signals, for example, a charge-coupled device (CCD) or complementary metal-oxide semiconductor (CMOS) image sensor. In some examples, the imaging device 306 can include one or more optical fibers. For example, the imaging device 102 may be a fiber optic bundle configured to transmit light representing an image from the distal end of the instrument 300 to an eyepiece and/or image sensor. Images captured by the imaging device 306 can then be transmitted as individual frames or series of successive frames (e.g., a video) to a computer system for storage or display. The images captured by the imaging device 306 may be used as vision data 92 by the localization system 90 to determine the estimated position for the instrument 100.

The robotic command and kinematics data 320 may be received from and/or generated by the instrument positioning device 308. As discussed above, robotic command and kinematics data 320 can include data related to physical movement of the instrument 300, such as data instructing instrument 300 to reach a specific anatomical site and/or change its orientation (e.g., with a specific pitch, roll, yaw, insertion, and/or retraction). The robotic command and kinematics data 320 can also include data representing mechanical movement the instrument 300, such as data related to motion of one or more pull wires or tendons that drive the actual movement or control the pose of the instrument 300.

The position sensor data 316, vision data 318, and robotic data 320 may be provided as data inputs to the processor 310. The processor 310 can executed the methods described herein to determine and output information regarding a location/position estimate 326 of the instrument 302. In the illustrated embodiment, information regarding the position estimate 326 is output to a display 324. The position estimate 326 may be stored in some embodiments. Implementing the methods described herein, the position estimate 326 may exhibit improved accuracy in cases where the instrument 300 experiences buckling or hysteresis.

3. Implementing Systems and Terminology

Implementations disclosed herein provide systems, methods and apparatus for determining instrument position with comparison of input data. Various implementations described herein provide for improved navigation and tracking of the instrument during a medical procedure.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that may be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that may be used to store desired program code in the form of instructions or data structures and that may be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "approximately" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic system comprising:
an instrument including an elongate shaft;
a robotic manipulator configured to manipulate the elongate shaft of the instrument; and
control circuitry communicatively coupled to the robotic manipulator and configured to:
    determine a first estimated position of at least a portion of the elongate shaft based on robotic command data, the first estimated position associated with a first confidence factor;
    determine a second estimated position of the portion of the elongate shaft based on position sensor data, the second estimated position associated with a second confidence factor;
    compare the first estimated position with the second estimated position;

adjust a weight of the first confidence factor or the second confidence factor based on the comparison of the first estimated position with the second estimated position; and
    generate a third estimated position of the portion of the elongate shaft based on the first confidence factor and the second confidence factor.

2. The robotic system of claim 1, wherein the control circuitry is further configured to:
detect a buckling condition of the elongate shaft based on the comparison of the first estimated position with the second estimated position.

3. The robotic system of claim 2, wherein detecting the buckling condition includes:
determining that the first estimated position indicates a first amount of motion of the elongate shaft;
determining that the second estimated position indicates a second amount of motion of the elongate shaft; and
determining that the first amount of motion is greater than the second amount of motion.

4. The robotic system of claim 2, wherein adjusting the weight of the first confidence factor comprises decreasing the weight of the first confidence factor relative to the second confidence factor.

5. The robotic system of claim 1, wherein the third estimated position is generated based on the second estimated position, and wherein the first confidence factor is set to zero so that the first estimated position is disregarded.

6. The robotic system of claim 1, wherein the control circuitry is further configured to:
detect a hysteresis condition of the elongate shaft based on the comparison of the first estimated position with the second estimated position.

7. The robotic system of claim 6, wherein detecting the hysteresis condition includes:
determining that the first estimated position indicates a first amount of motion of the elongate shaft;
determining that second estimated position indicates a second amount of motion of the elongate shaft; and
determining that the first amount of motion is less than the second amount of motion.

8. The robotic system of claim 1, wherein the control circuitry is further configured to:
determine a fourth estimated position of the portion of the elongate shaft based on image data from a camera associated with the elongate shaft; and
compare the fourth estimated position with at least one of the first estimated position or the second estimated position, wherein the third estimated position is based on the comparison of the fourth estimated position with the at least one of the first estimated position or the second estimated position.

9. The robotic system of claim 8, wherein the third estimated position is based on a weighted combination of the first estimated position, the second estimated position, and the fourth estimated position.

10. The robotic system of claim 1, wherein the robotic command data indicates at least one of a commanded insertion depth, a commanded articulation, or a roll angle of the elongate shaft executed by the robotic manipulator.

11. A robotic system comprising:
an instrument including an elongate shaft;
a robotic manipulator configured to manipulate the elongate shaft of the instrument; and
control circuitry communicatively coupled to the robotic manipulator and configured to:

determine a commanded motion of a distal end of the elongate shaft based on robotic command data, the commanded motion associated with a first confidence factor;

determine a sensed motion of the distal end of the elongate shaft based on position sensor data, the sensed motion associated with a second confidence factor;

compare the commanded motion with the sensed motion;

adjust a weight of the first confidence factor or the second confidence factor based on the comparison of the commanded motion with the sensed motion; and determine an occurrence of buckling of the elongate shaft or hysteresis of the elongate shaft based on the first confidence factor and the second confidence factor.

12. The robotic system of claim 11, wherein determining the occurrence of buckling of the elongate shaft includes:

detecting a buckling event when the commanded motion is greater than the sensed motion.

13. The robotic system of claim 11, wherein determining the occurrence of hysteresis of the elongate shaft includes:

detecting a hysteresis event when the sensed motion is greater than the commanded motion.

14. The robotic system of claim 11, wherein the robotic command data is associated with a command provided to the robotic manipulator prior to the determining of the sensed motion.

15. A method comprising:

determining a first estimated position of at least a portion of an elongate shaft of an instrument based on robotic command data, the first estimated position associated with a first confidence factor;

determining a second estimated position of the portion of the elongate shaft based on position sensor data, the second estimated position associated with a second confidence factor;

comparing the first estimated position with the second estimated position;

adjust a weight of the first confidence factor or the second confidence factor based on the comparison of the first estimated position with the second estimated position; and generating a third estimated position of the portion of the elongate shaft based on the first confidence factor and the second confidence factor.

16. The method of claim 15, further comprising:

detecting a buckling condition of the elongate shaft based on the comparison of the first estimated position with the second estimated position.

17. The method of claim 15, wherein the third estimated position is generated based on the second estimated position, and wherein the first confidence factor is set to zero so that the first estimated position is disregarded.

18. The method of claim 15, further comprising:

detecting a hysteresis condition of the elongate shaft based on the comparison of the first estimated position with the second estimated position.

19. The method of claim 15, further comprising:

determining a fourth estimated position of the portion of the elongate shaft based on image data from a camera associated with the elongate shaft; and comparing the fourth estimated position with at least one of the first estimated position or the second estimated position, wherein the third estimated position is based on the comparison of the fourth estimated position with the at least one of the first estimated position or the second estimated position.

20. The method of claim 15, wherein the robotic command data indicates at least one of a commanded insertion depth, a commanded articulation, or a roll angle of the elongate shaft executed by a robotic manipulator.

* * * * *